United States Patent
Wang et al.

(10) Patent No.: US 11,661,454 B2
(45) Date of Patent: May 30, 2023

(54) ANTI-VEGF-PD1 BISPECIFIC ANTIBODY WITH NOVEL STRUCTURE AND USE THEREOF

(71) Applicant: ANHUI BIOX VISION BIOLOGICAL TECHNOLOGY CO., LTD., Anhui (CN)

(72) Inventors: Guoxing Wang, Anhui (CN); Liansheng Cheng, Anhui (CN); Siyi Hu, Anhui (CN); Hong Yuan, Anhui (CN); Ting Wu, Anhui (CN); Li Fan, Anhui (CN)

(73) Assignee: ANHUI BIOX VISION BIOLOGICAL TECHNOLOGY CO., LTD., Anhui (CN)

( * ) Notice: Subject to any disclaimer, the term of this patent is extended or adjusted under 35 U.S.C. 154(b) by 201 days.

(21) Appl. No.: 16/980,853

(22) PCT Filed: Aug. 9, 2019

(86) PCT No.: PCT/CN2019/099989
§ 371 (c)(1),
(2) Date: Sep. 15, 2020

(87) PCT Pub. No.: WO2021/026685
PCT Pub. Date: Feb. 18, 2021

(65) Prior Publication Data
US 2021/0403563 A1    Dec. 30, 2021

(51) Int. Cl.
*C07K 16/28* (2006.01)
*C07K 16/22* (2006.01)
*A61K 39/00* (2006.01)

(52) U.S. Cl.
CPC .......... *C07K 16/2818* (2013.01); *C07K 16/22* (2013.01); *A61K 2039/505* (2013.01); *C07K 2317/24* (2013.01); *C07K 2317/31* (2013.01); *C07K 2317/622* (2013.01); *C07K 2317/624* (2013.01); *C07K 2317/64* (2013.01); *C07K 2317/70* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 10,617,755 B2 * | 4/2020 | Bais | A61K 39/39541 |
| 11,059,885 B2 * | 7/2021 | Lu | A61K 9/08 |
| 2019/0367617 A1 * | 12/2019 | Li | A61P 35/00 |

FOREIGN PATENT DOCUMENTS

| | | |
|---|---|---|
| CN | 105175544 | 12/2015 |
| CN | 105175545 | 12/2015 |
| CN | 109575140 | 4/2019 |
| JP | 2019506863 | 3/2019 |

OTHER PUBLICATIONS

"International Search Report (Form PCT/ISA/210) of PCT/CN2019/099989," dated Apr. 23, 2020, pp. 1-5.

* cited by examiner

*Primary Examiner* — Marianne P Allen
(74) *Attorney, Agent, or Firm* — JCIP Global Inc.

(57) ABSTRACT

The disclosure relates to an anti-VEGF-PD1 bispecific antibody with a novel structure and a use thereof, which belongs to the technical field of molecular immunology. The CDR-H1 in the heavy chain variable region of the antibody is an amino acid sequence expressed by SEQ ID NO: 1, the CDR-H2 is an amino acid sequence expressed by SEQ ID NO: 2, the CDR-H3 is an amino acid sequence expressed by SEQ ID NO: 3, and the CDR-L in the light chain variable region of the antibody is an amino acid sequence expressed by SEQ ID NO:4.

2 Claims, 10 Drawing Sheets
Specification includes a Sequence Listing.

SEQUENCE LISTING

```
<160> NUMBER OF SEQ ID NOS: 28

<210> SEQ ID NO 1
<211> LENGTH: 118
<212> TYPE: PRT
<213> ORGANISM: Artificial Sequence
<220> FEATURE:
<223> OTHER INFORMATION: Synthesized in the laboratory

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
                20                  25                  30

Asp Met Ser Trp Val Arg Gln Ala Pro Gly Lys Cys Leu Glu Trp Val
            35                  40                  45

Ala Thr Ile Ser Gly Gly Gly Arg Tyr Thr Tyr Tyr Pro Asp Ser Val
        50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Val Tyr Tyr Cys
                85                  90                  95

Ala Val Arg Tyr Gly Glu Thr Trp Phe Ala Tyr Trp Gly Gln Gly Thr
                100                 105                 110

Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthesized in the laboratory

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
                20                  25                  30

Leu Ala Trp Phe Gln Gln Lys Pro Gly Lys Ala Pro Lys Ser Leu Ile
            35                  40                  45

Tyr Arg Ala Asn Arg Leu Val Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Cys Gly Thr Lys Leu Glu Leu Lys
                100                 105
```

<210> SEQ ID NO 3
<211> LENGTH: 123
<212> TYPE: PRT
<213> ORGANISM: Artificial Sequence
<220> FEATURE:
<223> OTHER INFORMATION: Synthesized in the laboratory

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: Synthesized in the laboratory

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 5
<211> LENGTH: 354
<212> TYPE: DNA
<213> ORGANISM: Artificial Sequence
<220> FEATURE:
<223> OTHER INFORMATION: Synthesized in the laboratory

<400> SEQUENCE: 5

```
caggtgcagc tggtggagag tggaggagga ctggtccagc ctggaggctc tctgagactg      60
tcctgcgcag catccggatt cgccttttcc tcttacgaca tgtcctgggt gaggcaggca     120
```

```
ccaggcaagt gcctggagtg ggtagcaaca atctctggag gcggccggta cacctactat    180
cccgacagcg tgaagggcag gtttaccatc tctcgcgata acagcaagaa caatctgtat    240
ctgcagatga atagcctgcg ggccgaggat acagccgtgt actactgtgc cgtgagatac    300
ggcgagacct ggttcgccta ttggggccag ggcaccctgg tgaccgtgag ctcc          354
```

```
<210> SEQ ID NO 6
<211> LENGTH: 321
<212> TYPE: DNA
<213> ORGANISM: Artificial Sequence
<220> FEATURE:
<223> OTHER INFORMATION: Synthesized in the laboratory

<400> SEQUENCE: 6
gacatccaga tgacccagag ccccagcagc ctgagcgcca gcgtgggcga cagggtgacc     60
atcacctgca gggccagcca ggacatcaac acctacctgg cctggttcca gcagaagccc    120
ggcaaggccc ccaagagcct gatctacagg gccaacaggc tggtgagcgg cgtgcccagc    180
aggttcagcg gcagcggcag cggcaccgac ttcaccctga ccatcagcag cctgcagccc    240
gaggacatgg ccacctacta ctgcctgcag tacgacgagt tccccctgac cttcggctgc    300
ggcaccaagc tggagctgaa g                                              321
```

```
<210> SEQ ID NO 7
<211> LENGTH: 369
<212> TYPE: DNA
<213> ORGANISM: Artificial Sequence
<220> FEATURE:
<223> OTHER INFORMATION: Synthesized in the laboratory

<400> SEQUENCE: 7
gaggtgcagc tggtggagtc cggaggagga ctggtgcagc caggaggctc cctgaggctg     60
tcttgtgcag ccagcggcta caccttcaca aactatggaa tgaattgggt gcgccaggca    120
ccaggcaagg gcctggagtg ggtgggctgg atcaacacct acacaggcga gcctacctat    180
gccgccgact ttaagcggag attcacattt ccctggata cctctaagag cacagcctac    240
ctgcagatga acagcctgag ggcagaggac accgccgtgt actattgcgc caagtacccc    300
cactactatg gcagctccca ctggtatttc gacgtgtggg gccagggcac cctggtgaca    360
gtgagctcc                                                            369
```

```
<210> SEQ ID NO 8
<211> LENGTH: 321
<212> TYPE: DNA
<213> ORGANISM: Artificial Sequence
<220> FEATURE:
<223> OTHER INFORMATION: Synthesized in the laboratory

<400> SEQUENCE: 8
gacatccaga tgacacagag ccctagctcc ctgagcgcct ccgtgggcga ccgggtgacc     60
atcacatgct ctgccagcca ggatatctcc aactacctga attggtatca gcagaagccc    120
ggcaaggccc ctaaggtgct gatctacttc acctctagcc tgcactccgg cgtgcccagc    180
cggttcagcg gctctggcag cggcaccgac tttaccctga catctcctc tctgcagcca    240 gaggatttcg ccacatacta ttgtcagcag tattctaccg tgccctggac atttggccag    300
ggcacaaagg tggagatcaa g                                              321
```

```
<210> SEQ ID NO 9
```

<211> LENGTH: 732
<212> TYPE: PRT
<213> ORGANISM: Artificial Sequence
<220> FEATURE:
<223> OTHER INFORMATION: Synthesized in the laboratory

<400> SEQUENCE: 9

```
Met Glu Phe Gly Leu Ser Trp Val Phe Leu Val Ala Ile Leu Lys Gly
1               5                   10                  15
Val Gln Cys Gln Val Gln Leu Val Glu Ser Gly Gly Gly Leu Val Gln
            20                  25                  30
Pro Gly Gly Ser Leu Arg Leu Ser Cys Ala Ala Ser Gly Phe Ala Phe
        35                  40                  45
Ser Ser Tyr Asp Met Ser Trp Val Arg Gln Ala Pro Gly Lys Cys Leu
    50                  55                  60
Glu Trp Val Ala Thr Ile Ser Gly Gly Gly Arg Tyr Thr Tyr Tyr Pro
65                  70                  75                  80
Asp Ser Val Lys Gly Arg Phe Thr Ile Ser Arg Asp Asn Ser Lys Asn
                85                  90                  95
Asn Leu Tyr Leu Gln Met Asn Ser Leu Arg Ala Glu Asp Thr Ala Val
            100                 105                 110
Tyr Tyr Cys Ala Val Arg Tyr Gly Glu Thr Trp Phe Ala Tyr Trp Gly
        115                 120                 125
Gln Gly Thr Leu Val Thr Val Ser Ser Gly Gly Gly Ser Gly Gly Gly
    130                 135                 140
Gly Gly Ser Gly Gly Gly Gly Ser Gly Gly Gly Gly Ser Asp Ile Gln
145                 150                 155                 160
Met Thr Gln Ser Pro Ser Ser Leu Ser Ala Ser Val Gly Asp Arg Val
                165                 170                 175
Thr Ile Thr Cys Arg Ala Ser Gln Asp Ile Asn Thr Tyr Leu Ala Trp
            180                 185                 190
Phe Gln Gln Lys Pro Gly Lys Ala Pro Lys Ser Leu Ile Tyr Arg Ala
        195                 200                 205
Asn Arg Leu Val Ser Gly Val Pro Ser Arg Phe Ser Gly Ser Gly Ser
    210                 215                 220
Gly Thr Asp Phe Thr Leu Thr Ile Ser Ser Leu Gln Pro Glu Asp Met
225                 230                 235                 240
Ala Thr Tyr Tyr Cys Leu Gln Tyr Asp Glu Phe Pro Leu Thr Phe Gly
                245                 250                 255
Cys Gly Thr Lys Leu Glu Leu Lys Gly Gly Gly Ala Ser Gly Gly Gly
            260                 265                 270
Gly Ser Gly Gly Gly Gly Ser Glu Val Gln Leu Val Glu Ser Gly Gly
        275                 280                 285
Gly Leu Val Gln Pro Gly Gly Ser Leu Arg Leu Ser Cys Ala Ala Ser
    290                 295                 300
Gly Tyr Thr Phe Thr Asn Tyr Gly Met Asn Trp Val Arg Gln Ala Pro
305                 310                 315                 320
Gly Lys Gly Leu Glu Trp Val Gly Trp Ile Asn Thr Tyr Thr Gly Glu
                325                 330                 335
Pro Thr Tyr Ala Ala Asp Phe Lys Arg Arg Phe Thr Phe Ser Leu Asp
            340                 345                 350
Thr Ser Lys Ser Thr Ala Tyr Leu Gln Met Asn Ser Leu Arg Ala Glu
        355                 360                 365
Asp Thr Ala Val Tyr Tyr Cys Ala Lys Tyr Pro His Tyr Tyr Gly Ser
    370                 375                 380
```

```
Ser His Trp Tyr Phe Asp Val Trp Gly Gln Gly Thr Leu Val Thr Val
385                 390                 395                 400

Ser Ser Ala Ser Thr Lys Gly Pro Ser Val Phe Pro Leu Ala Pro Ser
            405                 410                 415

Ser Lys Ser Thr Ser Gly Gly Thr Ala Ala Leu Gly Cys Leu Val Lys
            420                 425                 430

Asp Tyr Phe Pro Glu Pro Val Thr Val Ser Trp Asn Ser Gly Ala Leu
        435                 440                 445

Thr Ser Gly Val His Thr Phe Pro Ala Val Leu Gln Ser Ser Gly Leu
    450                 455                 460

Tyr Ser Leu Ser Ser Val Val Thr Val Pro Ser Ser Leu Gly Thr
465                 470                 475                 480

Gln Thr Tyr Ile Cys Asn Val Asn His Lys Pro Ser Asn Thr Lys Val
                485                 490                 495

Asp Lys Lys Val Glu Pro Lys Ser Cys Asp Lys Thr His Thr Cys Pro
            500                 505                 510

Pro Cys Pro Ala Pro Glu Ala Ala Gly Gly Pro Ser Val Phe Leu Phe
        515                 520                 525

Pro Pro Lys Pro Lys Asp Thr Leu Met Ile Ser Arg Thr Pro Glu Val
    530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Arg Glu Glu Gln Tyr Asn Ser Thr Tyr Arg Val Val Ser Val Leu Thr
            580                 585                 590

Val Leu His Gln Asp Trp Leu Asn Gly Lys Glu Tyr Lys Cys Lys Val
        595                 600                 605

Ser Asn Lys Ala Leu Pro Ala Pro Ile Glu Lys Thr Ile Ser Lys Ala
    610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
        675                 680                 685

Phe Phe Leu Tyr Ser Lys Leu Thr Val Asp Lys Ser Arg Trp Gln Gln
    690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys
                725                 730

<210> SEQ ID NO 10
<211> LENGTH: 234
<212> TYPE: PRT
<213> ORGANISM: Artificial Sequence
<220> FEATURE:
<223> OTHER INFORMATION: Synthesized in the laboratory

<400> SEQUENCE: 10

Met Glu Thr Asp Thr Leu Leu Leu Trp Val Leu Leu Leu Trp Val Pro
1               5                   10                  15
```

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Ser Ala Ser Gln Asp
        35                  40                  45

Ile Ser Asn Tyr Leu Asn Trp Tyr Gln Gln Lys Pro Gly Lys Ala Pro
    50                  55                  60

Lys Val Leu Ile Tyr Phe Thr Ser Ser Leu His Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Ser
            100                 105                 110

Thr Val Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 2199
<212> TYPE: DNA
<213> ORGANISM: Artificial Sequence
<220> FEATURE:
<223> OTHER INFORMATION: Synthesized in the laboratory

<400> SEQUENCE: 11
atggagttcg gcctgagctg ggtgtttctg gtggccatcc tgaagggcgt gcagtgccag      60
gtgcagctgg tggagagtgg aggaggactg gtccagcctg gaggctctct gagactgtcc     120
tgcgcagcat ccggattcgc cttttcctct tacgacatgt cctgggtgag gcaggcacca     180
ggcaagtgcc tggagtgggt agcaacaatc tctggaggcg ccggtacac ctactatccc      240 gacagcgtga agggcaggtt taccatctct cgcgataaca gcaagaacaa tctgtatctg     300
cagatgaata gcctgcgggc cgaggataca gccgtgtact actgtgccgt gagatacggc     360
gagacctggt cgcctattg ggccagggc accctggtga ccgtgagctc ggaggagga       420 ggatccggag gaggaggaag cggaggagga ggatctggcg gcggcggctc tgacatccag     480
atgacccaga gccccagcag cctgagcgcc agcgtgggcg acagggtgac catcacctgc     540
agggccagcc aggacatcaa cacctacctg gcctggttcc agcagaagcc cggcaaggcc     600
cccaagagcc tgatctacag ggccaacagg ctggtgagcg gcgtgcccag caggttcagc     660
ggcagcggca gcggcaccga cttcaccctg accatcagca gcctgcagcc cgaggacatg     720
gccacctact actgcctgca gtacgacgag ttccccctga ccttcggctg cggcaccaag     780

```
ctggagctga agggcggcgg cgctagcggc ggaggaggca gcggaggagg gggatctgag    840
gtgcagctgg tggagtccgg aggaggactg gtgcagccag gaggctccct gaggctgtct    900
tgtgcagcca gcggctacac cttcacaaac tatggaatga attgggtgcg ccaggcacca    960
ggcaagggcc tggagtgggt gggctggatc aacacctaca caggcgagcc tacctatgcc   1020
gccgacttta gcggagatt cacatttcc ctggatacct ctaagagcac agcctacctg    1080
cagatgaaca gcctgagggc agaggacacc gccgtgtact attgcgccaa gtaccccac   1140
tactatggca gctcccactg gtatttcgac gtgtggggcc agggcaccct ggtgacagtg   1200
agctccgcca gcaccaaggg gccctccgtg tttcctctgg ccccatcctc taagagcacc   1260
tccggaggaa cagccgccct gggctgtctg gtgaaggatt acttccctga gccagtgaca   1320
gtgtcttgga acagcggcgc cctgacctcc ggagtgcaca catttccagc cgtgctgcag   1380
agctccggac tgtatagcct gtctagcgtg gtgaccgtgc cttcctctag cctgggcacc   1440
cagacatata tctgcaacgt gaatcacaag ccatccaata caaggtgga caagaaggtg   1500
gagcccaagt cttgtgataa gacccacaca tgcccaccat gtccagcacc tgaggccgcc   1560
ggcggaccta gcgtgttcct gtttcctcca aagccaaagg acaccctgat gatcagccgg   1620
accccagagg tgacatgcgt ggtggtggac gtgtcccacg aggaccccga ggtgaagttc   1680
aactggtacg tggatggcgt ggaggtgcac aatgccaaga ccaagcccg ggaggagcag   1740
tacaactcta cctatagagt ggtgagcgtg ctgacagtgc tgcaccagga ctggctgaac   1800
ggcaaggagt ataagtgcaa ggtgtctaat aaggccctgc cagccccat cgagaagacc   1860
atcagcaagg caaagggaca gcccagggag cctcaggtgt atacactgcc ccctagccgg   1920
gaggagatga ccaagaacca ggtgagcctg acatgtctgg tgaagggctt ctatcccagc   1980
gacatcgccg tggagtggga gtccaatggc cagcctgaga caattacaa gaccacacca   2040
cccgtgctgg actccgatgg ctctttctt ctgtattcca agctgaccgt ggataagagc   2100
cggtggcagc agggcaacgt gttttcttgt agcgtgatgc acgaggccct gcacaatcac   2160
tacacacaga agtccctgtc tctgagccct ggcaagtga                          2199

<210> SEQ ID NO 12
<211> LENGTH: 708
<212> TYPE: DNA
<213> ORGANISM: Artificial Sequence
<220> FEATURE:
<223> OTHER INFORMATION: Synthesized in the laboratory

<400> SEQUENCE: 12
atggagacag acacactcct gctatgggta ctgctgctct gggttccagg atccacaggc     60
gacatccaga tgacacagag ccctagctcc ctgagcgcct ccgtgggcga ccgggtgacc    120
atcacatgct ctgccagcca ggatatctcc aactacctga attggtatca gcagaagccc    180
ggcaaggccc ctaaggtgct gatctacttc acctctagcc tgcactccgg cgtgcccagc    240
cggttcagcg gctctggcag cggcaccgac tttaccctga caatctcctc tctgcagcca    300
gaggatttcg ccacatacta ttgtcagcag tattctaccg tgccctggac atttggccag    360
ggcacaaagg tggagatcaa gcgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
```
ctgagctcgc ccgtcacaaa gagcttcaac aggggagagt gctaatga 708

<210> SEQ ID NO 13
<211> LENGTH: 118
<212> TYPE: PRT
<213> ORGANISM: Artificial Sequence
<220> FEATURE:
<223> OTHER INFORMATION: Modified by female BALB/c mice

<400> SEQUENCE: 13

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Ser Arg Phe Gly Glu Ala Trp Phe Ala Tyr Trp Gly Gln Gly Thr
            100                 105                 110

Leu Val Thr Val Ser Ala
        115

<210> SEQ ID NO 14
<211> LENGTH: 107
<212> TYPE: PRT
<213> ORGANISM: Artificial Sequence
<220> FEATURE:
<223> OTHER INFORMATION: Modified by female BALB/c mice

<400> SEQUENCE: 14

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105

<210> SEQ ID NO 15
<211> LENGTH: 13
<212> TYPE: PRT
<213> ORGANISM: Artificial Sequence
<220> FEATURE:
<223> OTHER INFORMATION: Modified by female BALB/c mice

<400> SEQUENCE: 15

Ala Ala Ser Gly Phe Thr Phe Ser Ser Tyr Gly Met Ser

```
<210> SEQ ID NO 16
<211> LENGTH: 17
<212> TYPE: PRT
<213> ORGANISM: Artificial Sequence
<220> FEATURE:
<223> OTHER INFORMATION: Modified by female BALB/c mice

<400> SEQUENCE: 16

Thr Ile Ser Gly Gly Gly Ser Tyr Thr Tyr Tyr Pro Asp Ser Val Lys
1               5                   10                  15
Gly

<210> SEQ ID NO 17
<211> LENGTH: 11
<212> TYPE: PRT
<213> ORGANISM: Artificial Sequence
<220> FEATURE:
<223> OTHER INFORMATION: Modified by female BALB/c mice

<400> SEQUENCE: 17

Ala Ser Arg Phe Gly Glu Ala Trp Phe Ala Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Modified by female BALB/c mice

<400> SEQUENCE: 18

Lys Ala Ser Gln Asp Ile Asn Ser Tyr Leu Ser
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Modified by female BALB/c mice

<400> SEQUENCE: 19

Tyr Arg Ala Asn Arg Leu Val Asp
1               5

<210> SEQ ID NO 20
<211> LENGTH: 9
<212> TYPE: PRT
<213> ORGANISM: Artificial Sequence
<220> FEATURE:
<223> OTHER INFORMATION: Modified by female BALB/c mice

<400> SEQUENCE: 20

Leu Gln Tyr Asp Glu Phe Pro Leu Thr
1               5

<210> SEQ ID NO 21
<211> LENGTH: 118
<212> TYPE: PRT
<213> ORGANISM: Artificial Sequence
<220> FEATURE:
<223> OTHER INFORMATION: Synthesized in the laboratory

<400> SEQUENCE: 21
```

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ala Thr Ile Ser Gly Gly Gly Arg Tyr Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Val Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser
        115

<210> SEQ ID NO 22
<211> LENGTH: 13
<212> TYPE: PRT
<213> ORGANISM: Artificial Sequence
<220> FEATURE:
<223> OTHER INFORMATION: Synthesized in the laboratory

<400> SEQUENCE: 22

Ala Ala Ser Gly Phe Ala Phe Ser Ser Tyr Asp Met Ser
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthesized in the laboratory

<400> SEQUENCE: 23

Thr Ile Ser Gly Gly Gly Arg Tyr Thr Tyr Tyr Pro Asp Ser Val Lys
1               5                   10                  15

Gly

<210> SEQ ID NO 24
<211> LENGTH: 11
<212> TYPE: PRT
<213> ORGANISM: Artificial Sequence
<220> FEATURE:
<223> OTHER INFORMATION: Synthesized in the laboratory

<400> SEQUENCE: 24

Ala Asn Arg Tyr Gly Glu Ala Trp Phe Ala Tyr
1               5                   10

<210> SEQ ID NO 25
<211> LENGTH: 108
<212> TYPE: PRT
<213> ORGANISM: Artificial Sequence
<220> FEATURE:
<223> OTHER INFORMATION: Synthesized in the laboratory

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr

```
                20                  25                  30
Leu Ala Trp Phe Gln Gln Lys Pro Gly Lys Ala Pro Lys Ser Leu Ile
            35                  40                  45

Tyr Arg Ala Asn Arg Leu Val Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Ala Gly Thr Lys Leu Glu Leu Lys Arg
            100                 105

<210> SEQ ID NO 26
<211> LENGTH: 11
<212> TYPE: PRT
<213> ORGANISM: Artificial Sequence
<220> FEATURE:
<223> OTHER INFORMATION: Synthesized in the laboratory

<400> SEQUENCE: 26

Arg Ala Ser Gln Asp Ile Asn Thr Tyr Leu Ala
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthesized in the laboratory

<400> SEQUENCE: 27

Tyr Arg Ala Asn Arg Leu Val Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthesized in the laboratory

<400> SEQUENCE: 28

Leu Gln Tyr Asp Glu Phe Pro Leu Thr
1               5
```

ANTI-VEGF-PD1 BISPECIFIC ANTIBODY WITH NOVEL STRUCTURE AND USE THEREOF

CROSS-REFERENCE TO RELATED APPLICATION

This application is a 371 application of International PCT application serial no. PCT/CN2019/099989, filed on Aug. 9, 2019. The entirety of the above-mentioned patent application is hereby incorporated by reference herein and made a part of this specification.

SEQUENCE LISTING

The instant application contains a Sequence Listing which has been submitted electronically in ASCII text file format and is hereby incorporated by reference in its entirety. Said ASCII copy, created on Jul. 8, 2021, is named 100946_sequence_listing.txt and is 27,168 bytes in size.

BACKGROUND

Technical Field

The disclosure relates to an anti-VEGF-PD1 bispecific antibody with a novel structure, which belongs to the technical field of molecular immunology.

Description of Related Art

Vascular endothelial growth factor (VEGF), also known as vascular permeability factor (VPF), is a highly specific vascular endothelial cell growth factor that has the ability to promote vascular permeability, modification of extracellular matrix, migration of vascular endothelial cell, proliferation and vascularization. Vascular endothelial growth factor is a family, including VEGF-A, VEGF-B, VEGF-C, VEGF-D, VEGF-E and placental growth factor (PGF). Usually VEGF is VEGF-A. VEGF-A can promote the formation of new blood vessels and increase the permeability of blood vessels. VEGF-B plays a role in tumors that are formed by non-neovascularization. VEGF-C and VEGF-D play a role in the formation of new blood vessels and new lymphatic vessels in cancer tissues. VEGF-E is also a potential neovascularization factor. PGF promotes neovascularization, increases vascular permeability, and significantly increases the expression of PGF in experimental choroidal neovascularization. High-affinity receptors that specifically bind to vascular endothelial growth factor are called vascularendothelialgrowthfactorreceptor (VEGFR), and are mainly classified into 3 types, including VEGFR-1, VEGFR-2, and VEGFR-3. VEGFR-1 and VEGFR-2 are mainly distributed on the surface of tumor vascular endothelium, regulating tumor angiogenesis; VEGFR-3 is mainly distributed on the surface of lymphatic endothelium, regulating tumor lymphangiogenesis. VEGF is a highly conserved homodimeric glycoprotein. Two single chains with a molecular weight of 24 kDa each form a dimer with disulfide bonds. The monomers decomposed by VEGF are inactive, and the removal of N2 glycosyl group has no effect on biological effects, but may play a role in cell secretion. Due to different splicing methods for mRNA, at least five protein forms such as VEGF121, VEGF145, VEGF165, VEGF185, and VEGF206 are produced, wherein VEGF121, VEGF145, and VEGF165 are secreted soluble proteins that can directly act on vascular endothelial cells to promote vascular endothelial cell proliferation and increase vascular permeability. In 1990, Dr. Folkman of Harvard University proposed the famous Folkman theory that the growth of tumor tissue must rely on neovascularization to have sufficient oxygen and nutrients to keep growing, which is considered as the basis of clinical application of VEGF. Monoclonal antibody with combination of anti-VEGF and VEGFR can inhibit vascular endothelial growth factor and is used to treat various metastatic cancers.

Programmed death receptor 1 (PD-1) is an important immunosuppressive molecule, which is an immunoglobulin superfamily and a membrane protein of 268 amino acid residues, originally cloned from the cell hybridoma 2B4.11 of an apoptotic mouse T. Immunomodulation with PD-1 as a target has important significance in treating tumors, anti-infections, anti-autoimmune diseases and organ transplantation survival. Its ligand PD-L1 can also be used as a target, and the corresponding antibody can also play the same role. The combination of PD-1 and PD-L1 initiates the programmed death of T cells, allowing tumor cells to achieve tumor immune escape. PD-1 has at least two ligands, one is PD-L1 and the other one is PD-L2; PD-L1 has at least two ligands, one is PD-1 and the other one is CD80; PD-L2 has at least two ligands, one is PD-1, and the other one is RGMB. PD-L1/L2 is expressed in antigen-presenting cells, and PD-L1 is also expressed in various tissues. The combination of PD-1 and PD-L1 mediates the co-suppression signal of T cell activation, regulates T cell activation and proliferation, and performs the function of negative regulatory similar to CTLA-4. A Chinese-American scientist's (Lie-ping Chen) lab first discovered that PD-L1 is highly expressed in tumor tissues and has the function of regulating tumor-infiltrating on CD8 T cells. Therefore, immunomodulation having PD-1/PD-L1 as target is of great significance to treat tumors. In recent years, various anti-PD-1/PD-L1 antibodies have been rapidly developed in clinical studies of tumor immunotherapy. Currently, Pembrolizumab and Nivolumab have been approved by the FDA for treating advanced melanoma. Moreover, recently Nivolumab has also been approved by the FDA in the US for treating advanced squamous non-small cell lung cancer. In addition, MPDL3280A (anti-PD-L1 monoclonal antibody), Avelumab (anti-PD-L1 monoclonal antibody), etc. have also been involved in multiple clinical studies on advanced cancers, covering non-small cell carcinoma, melanoma, bladder cancer and other tumor types. Due to the prospects in treating broad-spectrum anti-tumor and amazing efficacy of PD-1 antibodies, the industry generally believes that antibodies directed at the PD-1 channel will make a breakthrough in the treatment of various tumors: for the treatment of non-small cell lung cancer, kidney cell cancer, ovarian cancer, melanoma, leukemia, anemia, etc. On the American Cancer Society (AACR) annual meeting and the American Society of Clinical Oncology (ASCO) annual meeting held in 2012 and 2013, the data related to clinical efficacy of PD-1 antibody drugs was revealed, and then PD-1 antibodies became the most popular antibody drugs for research conducted by drug manufacturers.

A bifunctional antibody is a bispecific antibody, which is a non-natural antibody whose two arms that bind to an antigen have different specificities. Bifunctional antibodies are usually constructed by using biological methods and chemical cross-linking methods. With the development of antibody engineering and molecular biology techniques, a new type of method for constructing bifunctional antibodies, genetic engineering method, has been developed in recent years. Using genetic engineering method can not only construct bifunctional antibodies with multiple functions and multiple uses, but also make the construction of humanized bifunctional antibodies a reality. As a new secondary guidance system, bifunctional antibody has potential application value in clinical treatment. On Dec. 3, 2014, the FDA in the US approved the launch of bispecific antibody Blincyto (Blinatumomab) developed by Amgen for use in the treatment of acute lymphocytic leukemia. Blinatumomab is a bispecific antibody for CD19 and CD3. Blincyto(Blinatumomab) is the first bispecific antibody approved by the FDA in the US. Currently, there are more than 40 types of bifunctional antibody developed, but due to the problems of low production efficiency and poor pharmacokinetic performance, the development of bispecific antibodies has been difficult.

Chinese patent application number 2015106924845.5, entitled "Anti-VEGF-PD1 bifunctional antibody and its application", provides an anti-VEGF-PD1 bifunctional antibody, which has a skeleton based on PD1 antibody, and the VEGF antibody is formed by bonding with single chains. The disclosure is based on this bifunctional antibody to optimize the structure and sequence.

SUMMARY

The purpose of the disclosure is to provide a stable, novel anti-VEGF-PD1 bispecific antibody Ps3Vm. This antibody has a high affinity and high specificity, can specifically differentiate target VEGF from target PD1, solve the defects that current antibodies have only a single effect and cannot adapt to complex diseases.

The disclosure is realized through the following technical solution:

An anti-VEGF-PD1 bispecific antibody Ps3Vm with a novel structure is provided, wherein CDR-H1 in the heavy chain variable region of the antibody is the amino acid sequence expressed by SEQ ID NO: 1, CDR-H2 is the amino acid sequence expressed by SEQ ID NO: 2 and CDR-H3 is the amino acid sequence expressed by SEQ ID NO: 3; and the CDR-L in the light chain variable region of the antibody is the amino acid sequence expressed by SEQ ID NO: 4.

Preferably, the CDR-H1 in the heavy chain variable region of the antibody is the nucleotide sequence expressed by SEQ ID NO: 5, CDR-H2 is the nucleotide sequence expressed by SEQ ID NO: 6, and CDR-H3 is the nucleotide sequence expressed by SEQ ID NO: 7; and CDR-L in the light chain variable region of the antibody is the nucleotide sequence expressed by SEQ ID NO: 8.

Preferably, the heavy chain constant region sequence of the antibody is the heavy chain constant region sequence of humanized IgG1, and the light chain constant region sequence is the light chain constant region sequence of humanized κ antibody.

Preferably, the heavy chain amino acid sequence of the antibody is expressed by SEQ ID NO: 9.

Preferably, the light chain amino acid sequence of the antibody is expressed by SEQ ID NO: 10.

Preferably, the heavy chain nucleotide sequence of the antibody is expressed by SEQ ID NO: 11.

Preferably, the light chain nucleotide sequence of the antibody is expressed by SEQ ID NO: 12.

A pharmaceutical composition comprising the above-mentioned antibody and a pharmaceutically acceptable carrier.

The use of the above-mentioned antibodies in the preparation of drugs that inhibit or neutralize the activity of VEGF and PD1.

Preferably, the drug that inhibits or neutralizes the activity of VEGF and PD1 is used to treat cancer.

The advantageous effect of the invention is that:

The bispecific antibody Ps3Vm can effectively bind to PD-1 and VEGF protein, and can effectively compete with PDL-1 to bind to PD-1 protein and compete with VEGF-A to bind to VEGF protein, while can effectively stimulate T cells to function and secrete cytokines IL-2 and IFN-γ. In contrast, the isotype control antibody cannot promote proliferation of T cells and secretion of IL-2 and IFN-γ. In addition, the bispecific antibody Ps3Vm can also significantly inhibit the growth of tumors in mice and has the best results in experiments.

DESCRIPTION OF THE EMBODIMENTS

In order to make the disclosure more comprehensible, the disclosure will be further described below in conjunction with the embodiments and accompanying drawings. The following embodiments are only to illustrate the disclosure but not to limit it. The materials, reagents, instruments and methods used in the following examples are all conventional materials, reagents, instruments and methods in the art unless otherwise specified, and can be obtained through commercial channels.

Example 1 Preparation of PD1 and VEGF Antigens and Antibodies

1. Construction of Expression Vector for PD-1 Antigen

In the cDNA of human PD-1 synthesized by Kingsray Corporation in Nanjing, the GeneID is 5133 and the cDNAID is NM_005018.2. After synthesizing the PD-1 gene in the extracellular region, an Fc purification tag was added to obtain PD-1-mFc, and Xba I was introduced at both ends. Two restriction enzyme splice sites of Bam HI were connected to the pTT5 expression plasmid, which was verified by sequencing. The sequenced plasmid was transfected into Trans10 (purchased from Beijing Quanshijin Biotechnology Co., Ltd.), and the single clone was picked and inoculated into 1 liter of LB liquid medium. When the $OD_{600}$ was 1, the cells were collected by centrifugation, and a plasmid maxiprep kit (purchased from Qiagen) was used to extract the plasmid.

2. Construction of Expression Vector for VEGF Antigen

The amino acid corresponding to the gene VEGF (NCBI Gene ID: 7422) was integrated with the Fc protein fragment mFc (Ig gamma-2A chain C region) of IgG of the mouse to obtain VEGF-mFc. In order to improve the expression efficiency of the target gene in the 293F cell expression system, the sequence was optimized, and Xba I was introduced at both ends. Two restriction enzyme splice sites of Bam HI were connected to the pTT5 expression plasmid, which was verified by sequencing. The sequenced plasmid was transfected into Trans10 (purchased from Beijing Quanshijin Biotechnology Co., Ltd.), and the single clone was picked and inoculated into 1 liter of LB liquid medium. When the $OD_{600}$ was 1, the cells were collected by centrifugation, and a plasmid maxiprep kit (purchased from Qiagen) was used to extract the plasmid.

3. Expression and Purification of PD-1 and VEGF Antigens

Figure 1:
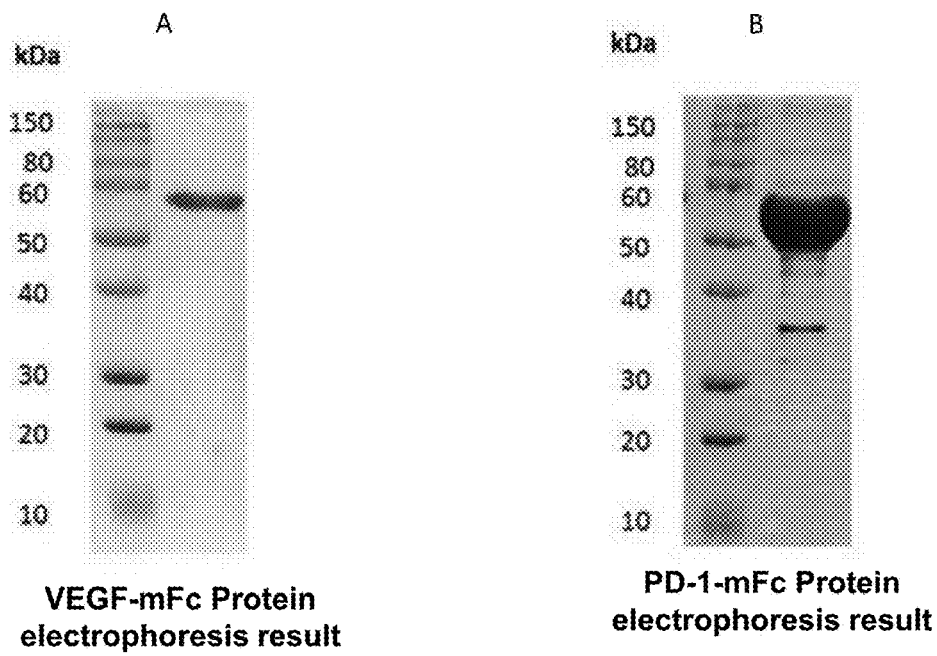
FIG. 1 is a graph showing a SDS-PAGE electrophoresis result of PD-1 and VEGF antigen (where A is VEGF antigen; B is PD-1 antigen).

Transfect 293F cells (purchased from Invitrogen) with the correct expression vector identified by sequencing, which was conducted at a temperature of 37 degrees with 5% of $CO_2$, and culture at 130 rpm/min for 7 days. Then, the supernatant was collected by centrifugation. The supernatant was centrifuged at 4000 rpm for 10 min, and then filtered with a 0.45 μm filter membrane; the filtrate was added with 400 mM of NaCl; and the pH was adjusted to 8.0. After the sample was filtered again through a 0.2 μm filter membrane, load the sample to a 5 mL HiTrap Protein A column equilibrated with PBS (137 mM of NaCl, 2.7 mM of KCl, 10 mM of $Na_2HPO_4$, 2 mM of $KH_2PO_4$, pH7.4). After the sample was loaded, use PBS for washing; the flow rate was 5 mL/min, and the UV monitoring result was at the standard level. Buffer B (1M Glycine, pH 3.5) was eluted at a flow rate of 1 mL/min. The flow-out peak was collected and neutralized with Tris to pH 7.5, and subjected to SDS-PAGE detection. The SDS-PAGE electrophoresis result is as shown in FIG. 1. The elution peak was concentrated and changed into PBS with an ultrafiltration concentration tube, thereby obtaining an antigen.

4. Construction of Anti-PD1 Humanized Antibody (1) Antigen-Immunized Mice and Hybridoma Screening In this experiment, three 8-week-old female BALB/c mice were selected, and the mice were immunized with a mixture of PD-1 extracellular domain antigen and Freund's complete adjuvant by intraperitoneal injection; the process was performed once a week in a total of 3 times. One week after the last immunization, the serum titers of the mice were measured. After the conditional titers were greater than 8K, the immunization was boosted once. The result showed that all 3 mice met the titers (the dilution value corresponding to the $OD_{450}$ value greater than 2 times the negative control and greater than 0.25 is the titer of the antibody, and the requirement is met as long as the titer is greater than or equal to 8K). After 3 days, the mice were sacrificed, the spleens of the mice were taken, and the spleen cell population was obtained after grinding. The ELISA test results of mouse serum titer are shown in Table 1.

TABLE 1

| Serial number of mice/ | ELISA detection of 20871 mouse immune serum | | | | | | | |
|---|---|---|---|---|---|---|---|---|
| | Dilution | | | | | | | |
| comparison | 1K | 2K | 4K | 8K | 16K | 32K | 64K | 128K |
| M1 | 1.23 | 1.04 | 0.508 | 0.427 | 0.281 | 0.189 | 0.103 | 0.067 |
| M2 | 1.124 | 1.01 | 0.861 | 0.546 | 0.294 | 0.171 | 0.127 | 0.094 |
| M3 | 1.254 | 1.149 | 0.918 | 0.545 | 0.325 | 0.18 | 0.116 | 0.088 |
| Positive control | | | | 2.549 | | | | |
| Negative control | | | | 0.048 | | | | |

The B cells of anti-human PD-1 antibody were screened by flow cytometry (FACS), placed in RPMI1640 medium, added with myeloma cells (SP2/0) and mixed, and cell integration was performed using 50% PEG solution. The integrated cells were appropriately diluted, divided and cultured in multiple 96-well culture plates, and HAT selective medium was added to kill unintegrated B cells and myeloma cells to obtain hybridoma cells. After cultured for 2 weeks, the 96-well plate cell culture supernatant was collected, combined with PD-1 antigen-coated 96-well microplate for 1 hour, added with anti-mouse/HRP secondary antibody and incubated for 1 hour, and finally added with TMB color reagent for 10 minutes. The light absorption value at 450 nm was measured with a microplate reader, and the hybridoma cells with binding activity to PD-1 were selected (primary screening: 12 pieces of 96-well plates to obtain 42 wells with OD value ≥0.5). Subsequently, flow cytometry (FACS) screening was performed to select hybridoma cells with PD-1/PD-L1 blocking activity. Then sub-cloning by limiting dilution method was carried out, and the cells with limited dilution were cultured in 96-well plates. When the clones grew to ⅙ of the full wells, the monoclones and polyclones were labeled, and the monoclones were detected by ELISA. After the detection, the monoclone with the highest OD value was then diluted into 96-well plates and subcloned again as described above. This process was repeated several times until the positive well ratio was 100%. The plant was successfully constructed, and an anti-PD-1 mouse monoclonal antibody cell strain was finally obtained. The result of subcloning by limiting dilution method is shown in Table 2, and the result of affinity identification is shown in Table 3.

TABLE 2

Positive clone well plate position

| Serial number | Positive clone | 96-well plate | 384-well plate | OD value |
|---|---|---|---|---|
| 1 | 2G8-1N8 | 2G8 | 1N8 | 1.022 |

TABLE 3

Affinity identification

| | | antigen 0.1 µg/mL | | | antigen 0.01 µg/mL | | | antigen 0.001 µg/mL | | |
|---|---|---|---|---|---|---|---|---|---|---|
| Plate position | Serial number | Dilution 1:3 | Dilution 1:9 | Dilution 1:27 | Dilution 1:3 | Dilution 1:9 | Dilution 1:27 | Dilution 1:3 | Dilution 1:9 | Dilution 1:27 |
| 1N8 | 1 | 0.98 | 0.837 | 0.793 | 0.124 | 0.181 | 0.108 | 0.11 | 0.149 | 0.11 |

(2) Anti-PD-1 Murine Antibody Variable Region Gene Retrieval

The anti-PD-1 hybridoma clones were selected, the total RNA was extracted using the Trizol method, and reverse transcription PCR was performed using antibody-specific (Isotype) specific primers or universal primers to respectively argument genes in the antibody light chain variable region (VL) and heavy chain variable region (VH), then connected to cloning vectors for DNA sequencing analysis. Finally, the complete DNA sequences of VL and VH were obtained and translated into corresponding amino acid sequences. The amino acid sequences of the heavy chain and light chain of the anti-PD-1 murine antibody are SEQ ID NO: 13-14 respectively; wherein, the CDR-H1, CDR-H2 and CDR-H3 amino acid sequences in the heavy chain variable region are SEQ ID NO: 15-17 respectively, the CDR-L1, CDR-L2 and CDR-L3 amino acid sequences in the light chain variable region are SEQ ID NO: 18-20 respectively.

(3) Humanized Transformation of Variable Region Gene of Anti-PD-1 Murine Monoclonal Antibody (a) Humanization of Heavy Chain First, Ig Blast (http://www.ncbi.nlm.nih.gov/igblast) was used to analyze human germline genes with high homology to the VH gene of the mouse PD-1 antibody. The result showed that the heavy chain IGHV3-23 had 83% homology at the amino acid level, so it was selected as a candidate gene template for the heavy chain variable region. The CDR-H1, CDR-H2 and CDR-H3 of the mouse PD-1 antibody were numbered according to the Kabat numbering rule, and the corresponding CDR region amino acid sequence was introduced into the framework region of IGHV3-23. The amino acid No. 49 (S->T) and No. 78 (T->N) in the framework region were back-mutated to the original sequence of mouse PD-1 antibody. Then, the heavy chain CDR H1 No. 33 (G->D) and H2 No. 56 (S->R) were subjected to additional mutations, thereby completing the humanization of the heavy chain variable region. The heavy chain amino acid sequence of the anti-PD-1 humanized antibody is SEQ ID NO: 21; wherein, the CDR-H1, CDR-H2, and CDR-H3 amino acid sequences of the heavy chain variable region are SEQ ID NO: 22-24, respectively.

(b) Humanization of Light Chain

First, Ig Blast (http://www.ncbi.nlm.nih.gov/igblast) was used to analyze human germline genes with high homology to the VL gene of the mouse PD-1 antibody. The result showed that the light chain IGKV1-16 had 86% homology at the amino acid level, so it was selected as a candidate gene template for the light chain variable region. The CDR-L1, CDR-L2 and CDR-L3 of the mouse PD-1 antibody were numbered according to the Kabat numbering rule, and the corresponding CDR region amino acid sequence was introduced into the framework region of IGKV1-16. The amino acid No. 83 (F->M) in the framework region was back-mutated to the original sequence of mouse PD-1 antibody. Then, the light chain CDR L1 No. 31 (S->T) and No. 34 (S->A), L2 No. 56 (D->L) were additionally mutated to complete humanization of the light chain variable region. The light chain amino acid sequence of the anti-PD-1 humanized antibody is SEQ ID NO: 25; wherein, the CDR-L1, CDR-L2 and CDR-L3 amino acid sequences of the light chain variable region are SEQ ID NO: 26-28, respectively.

(4) Affinity Maturation of Anti-PD-1 Humanized Antibodies

Figure 2:
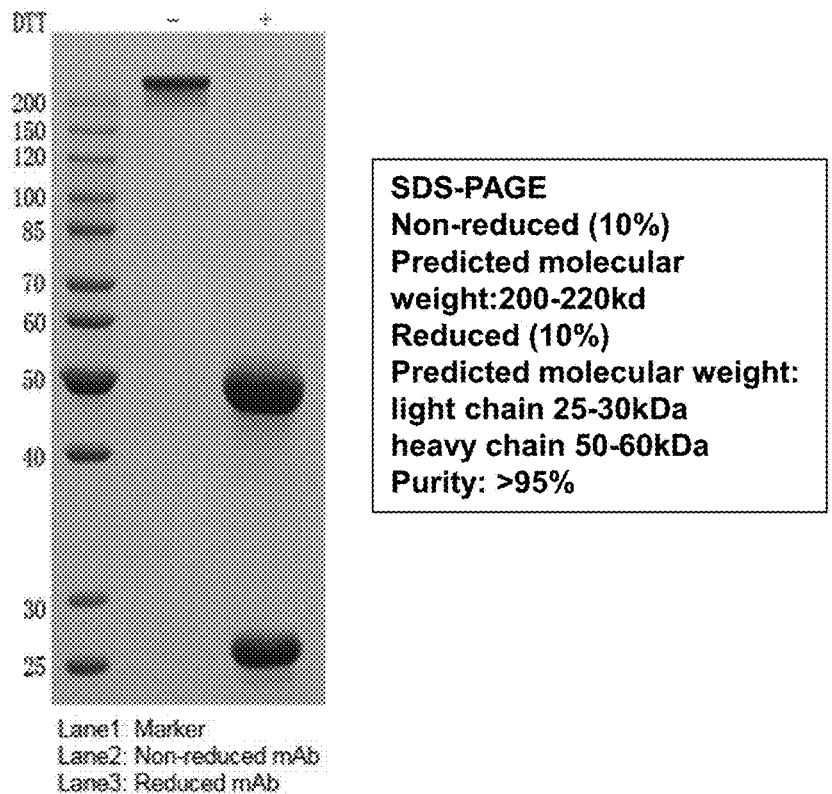
FIG. 2 is a graph showing an electrophoretic detection result of anti-PD-1 humanized antibody PDAB.

An antibody mutant library was designed for the five CDR regions (L1, L3, H1, H2, and H3) of the anti-PD-1 humanized antibody, and the mutation sites covered all non-conserved sites of the CDR regions. A single chain antibody (scFv) gene was obtained by SOE-PCR reaction, after DNA gel recovery and digestion, it was connected with the digested pCANTAB-5E phage display vector to electrotransform TG1 competent bacteria to obtain 5 CDR-containing mutations single chain antibody library. By infecting M13KO7 helper phage to produce recombinant phage, a total of three rounds of elutriation were performed to retain and enrich antibody-binding mutants with strong binding ability. In each round of elutriation, the recombinant phage and the biotin-labeled recombinant human PD-1 antigen were combined for 2 hours, then streptavidin magnetic beads were added for 30 minutes, and 2% of TPBS, 1% of TPBS and PBS were used in sequence for washing for 5 times, 5 minutes per washing. After the elutriation, TG1 cells were immediately used for infection for the next round of preparation of recombinant phage. After three rounds of elutriation, the enriched TG1 monoclone were selected to prepare the recombinant phage supernatant, which was combined with a 96-well microtiter plate coated with 1 µg/mL PD-1 antigen for 1 hour, added with M13/HRP secondary antibody and incubated for 1 hour, and finally added with OPD to carry out a color reaction for 10 minutes. The light absorption value at 490 nm was measured with a microplate reader. After analyzing the data, calculate the relative affinity of antibody-containing mutants, and select 3, 6, and 5 clones with significantly improved affinity from the L3, H1, and H3 mutant libraries, respectively, and finally select one clone PDAB with the highest affinity from the H3 mutant library for the next study. The electrophoresis result is shown in FIG. 2.

5. Construction of Anti-VEGF Humanized Antibody

Figure 3:
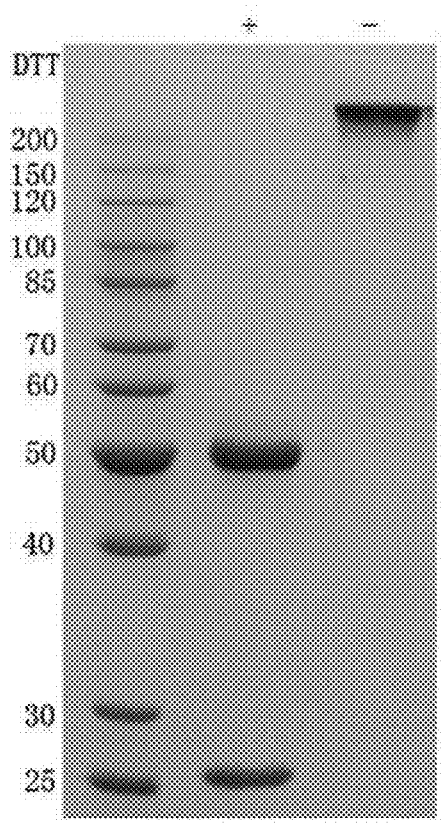
FIG. 3 is a graph showing an electrophoretic detection result of anti-VEGF humanized antibody Avastin.

The anti-VEGF humanized antibody used in this experiment was bevacizumab (Avastin, bevacizumab) launched by Roche (Genentech) in 2004. The antibody sequence (CN101210051A) was obtained from a public protein sequence website such as a patent website. The cDNA of the light chain and the heavy chain of VEGF antibody was artificially synthesized, and the synthesized cDNA was cloned into the pTT5 plasmid, and the plasmid construction was verified by sequencing. The sequenced plasmid was transfected into Trans10 (purchased from Beijing Quanshijin Biotechnology Co., Ltd.), and the single clone was picked and inoculated into 1 liter of LB liquid medium. When the $OD_{600}$ was 1, the cells were collected by centrifugation, and a plasmid maxiprep kit (purchased from Qiagen) was used to extract the plasmid. The VEGF heavy chain expression vector and light chain expression vector (1:1) identified by sequencing were co-transfected into 293F cells, which was performed at a temperature of 37 degrees with 5% of $CO_2$, and cultured at 130 rpm/min for 7 days. The supernatant was collected by centrifugation. The supernatant was centrifuged at 4000 rpm for 10 min, and filtered with a 0.45 μm filter membrane, and the filtrate was collected; the filtrate was added with 400 mM of NaCl; the pH was adjusted to 8.0. After the sample was filtered again through a 0.2 μm filter membrane, the sample was loaded to a 5 mL HiTrap MabSelect column (purchased from GE) that had been equilibrated with PBS (137 mM of NaCl, 2.7 mM of KCl, 10 mM of $Na_2HPO_4$, 2 m of $MKH_2PO_4$, pH7.4). After the sample was completely loaded, rinse with PBS at a flow rate of 5 mL/min, and the UV monitoring result is at a standard level. Buffer B (1M Glycine, pH3.5) was eluted at a flow rate of 1 mL/min. The flow-out peak was collected and neutralized with Tris to pH7.5, and subjected to SDS-PAGE detection. The SDS-PAGE non-reducing electrophoresis detection result is shown in FIG. 3. The elution peak was concentrated with an ultrafiltration concentration tube, and the solution was changed into PBS with a desalting column to obtain antibody VEGF protein.

Example 2 Preparation of Candidate Bispecific Antibodies

Figure 4:
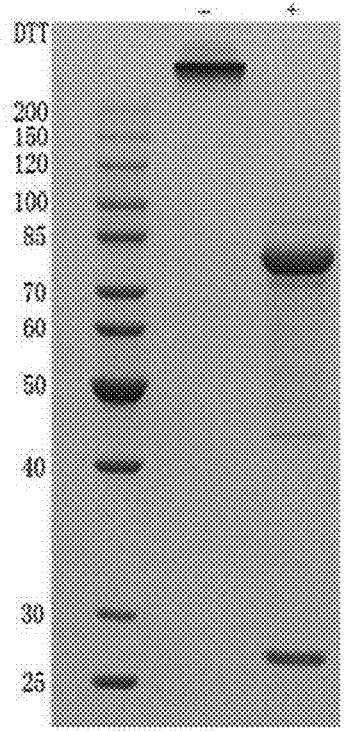
FIG. 4 is a graph showing an electrophoretic detection result of the bispecific antibody A3P4.
Figure 5:
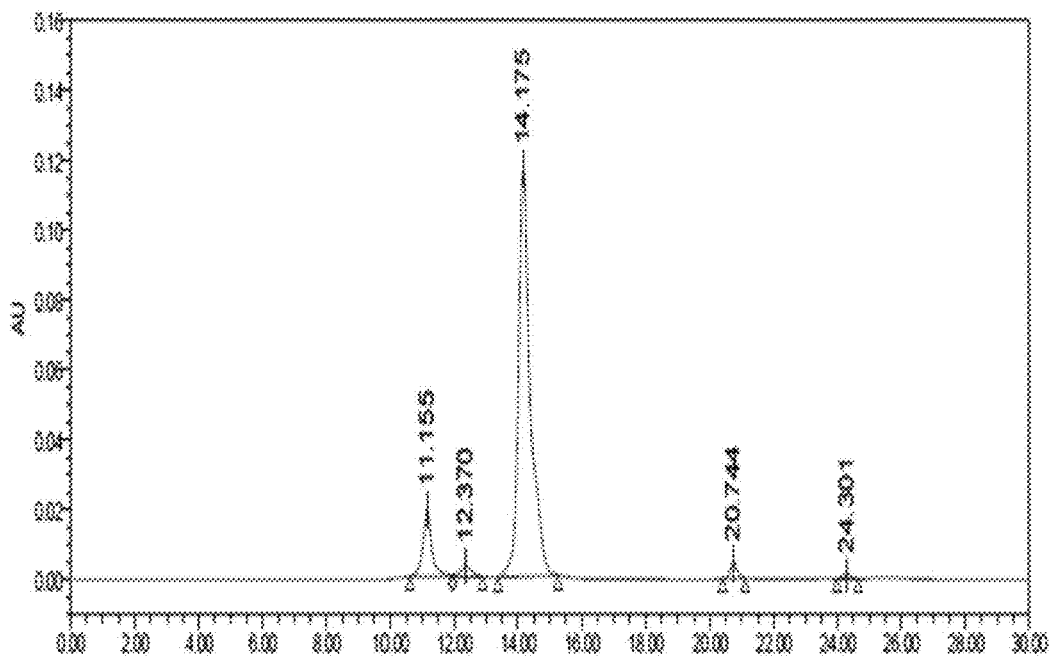
FIG. 5 is a graph showing a SEC detection result of the bispecific antibody A3P4.

1. Preparation of scFv-VEGF-Linker-PD1-H Chain Structure Bispecific Antibody (A3P4):

On the basis of existing anti-VEGF humanized antibodies, the heavy chain and light chain variable region genes are extracted and connected with peptides to form a single chain antibody scFv-VEGF. The scFv-VEGF was cloned into the N-terminus of the anti-PD1 antibody heavy chain to construct a bispecific antibody with scFv-VEGF-linker-PD1-H chain structure. The heavy chain expression vector and the light chain expression vector of anti-PD1 antibody were co-transformed into 293F cells, and the supernatant was collected and purified. SDS-PAGE was used to identify molecular weight and purity (see FIG. 4). By using SEC, it was detected that there are more antibody dimers in this sequence (see FIG. 5).

Figure 6:
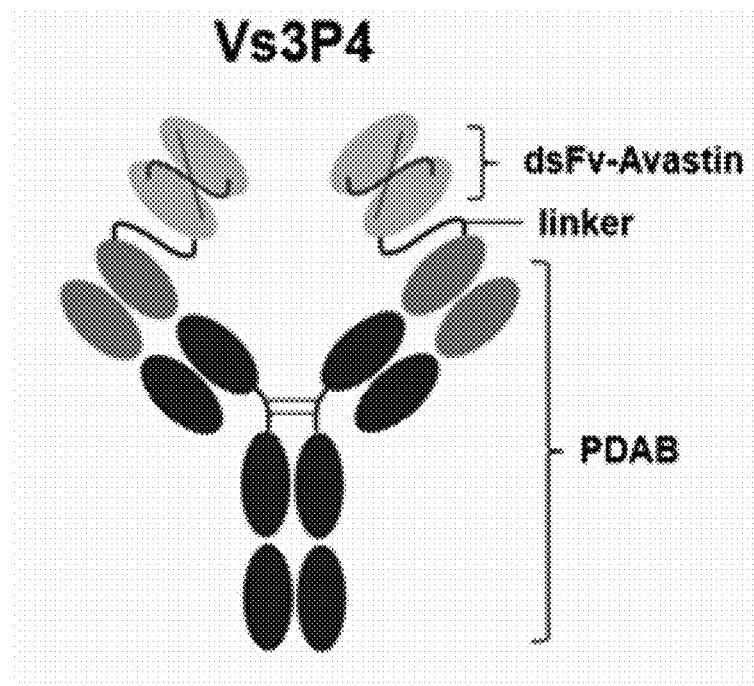
FIG. 6 is a schematic view of a protein structure of the bispecific antibody Vs3P4.
Figure 7:
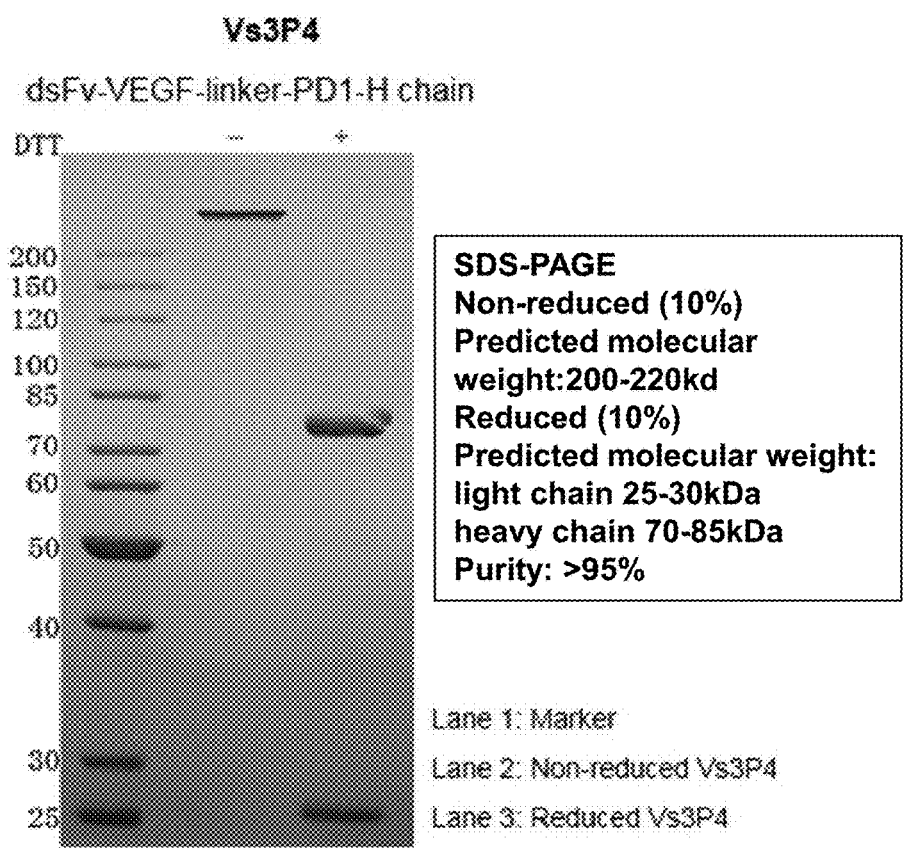
FIG. 7 is a graph showing an electrophoretic detection result of the bispecific antibody Vs3P4.
Figure 8:
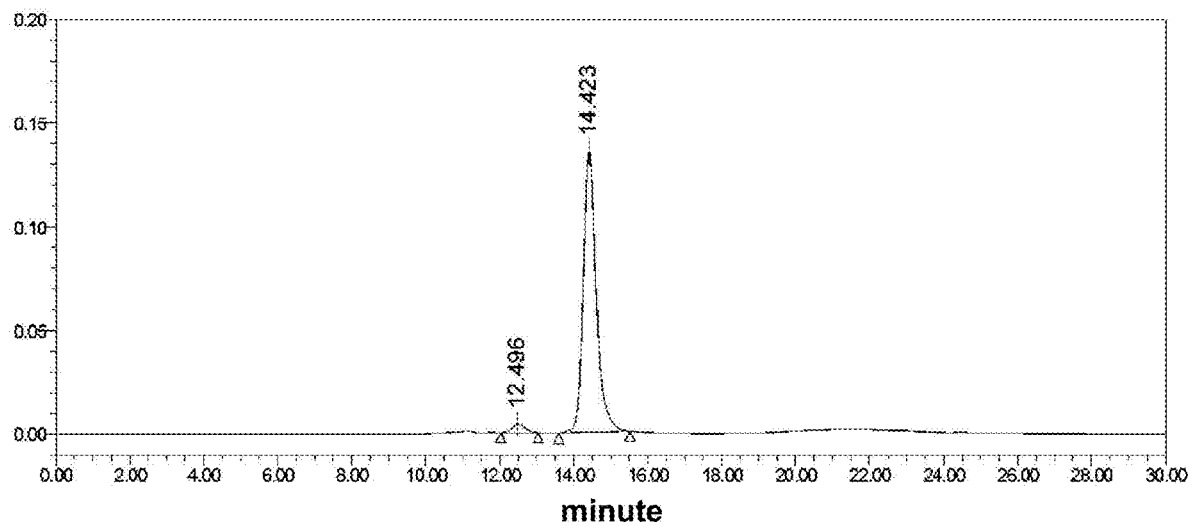
FIG. 8 is a graph showing a SEC detection result of the bispecific antibody Vs3P4.

2. Preparation of dsFv-VEGF-Linker-PD1-H Chain Structure Bispecific Antibody (Vs3P4):

On the basis of the original experiment, the new structure is redesigned. The heavy chain and light chain variable region genes of anti-VEGF humanized antibody were extracted and VH44cys and VL100cys mutations were performed (intra-chain disulfide bonds were increased to improve aggregation), and peptide chains were connected to form single-chain antibody dsFv-VEGF. The dsFv-VEGF was cloned into the N-terminus of the anti-PD1 antibody heavy chain to construct a bispecific antibody with a dsFv-VEGF-linker-PD1-H chain structure (see FIG. 6). The heavy chain expression vector and anti-PD1 antibody light chain expression vector were co-transformed into 293F cells, and the supernatant was collected and purified. SDS-PAGE was used to identify molecular weight and purity (see FIG. 7), and SEC detection was performed (see FIG. 8).

Figure 9:
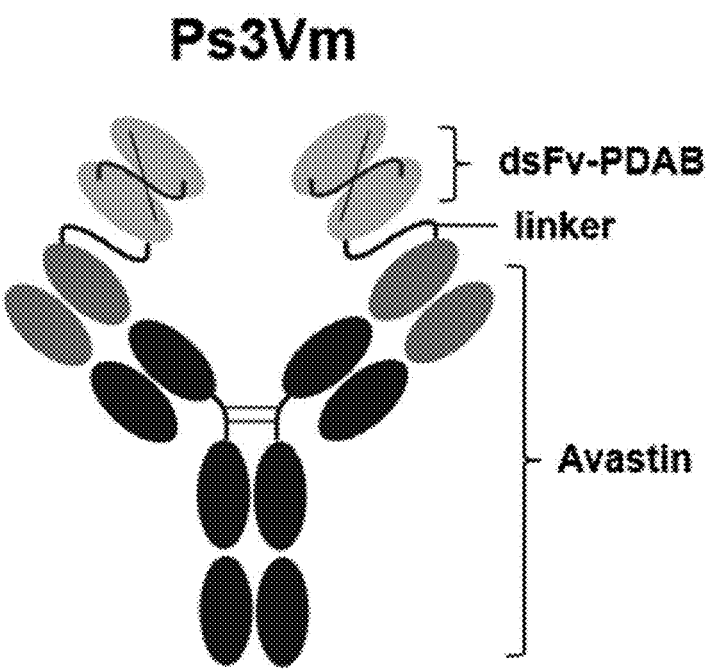
FIG. 9 is a schematic view of a protein structure of the bispecific antibody Ps3Vm.
Figure 10:
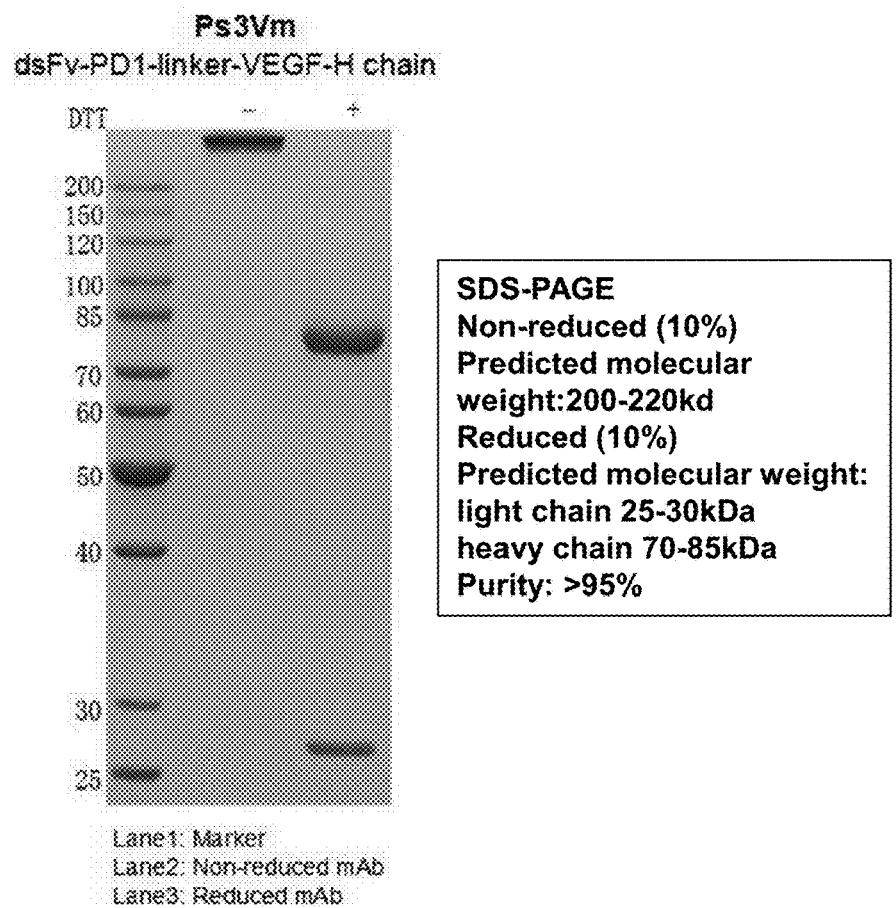
FIG. 10 is a graph showing an electrophoretic detection result of the bispecific antibody Ps3Vm.
Figure 11:
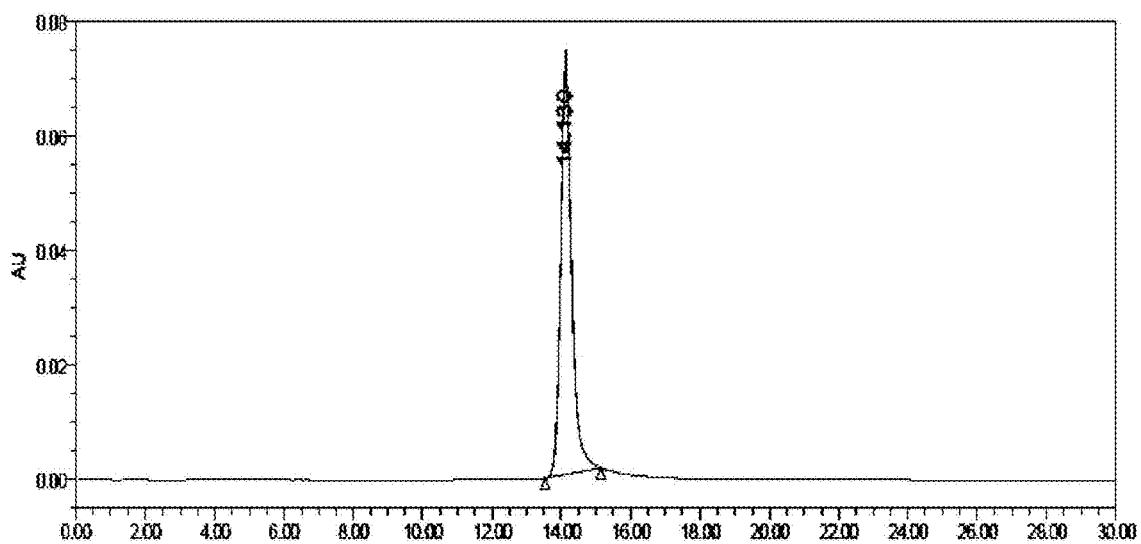
FIG. 11 is a graph showing a SEC detection result of the bispecific antibody Ps3Vm.

3. Preparation of dsFv-PD1-Linker-VEGF-H Chain Structure Bispecific Antibody (Ps3Vm):

This is the third structural optimization design. On the basis of the existing anti-PD1 humanized antibody, the heavy chain and light chain variable region genes were extracted and VH44cys and VL100cys mutations were performed (intra-chain disulfide bonds were increased to improve aggregation), and peptide chains were connected to form single-chain antibody dsFv-PD1. The dsFv-PD1 was cloned into the N-terminus of the anti-VEGF antibody heavy chain to construct a bispecific antibody with a dsFv-PD1-linker-VEGF-H chain structure (see FIG. 9). The heavy chain expression vector and anti-VEGF antibody light chain expression vector were co-transformed into 293F cells, and the supernatant was collected and purified. SDS-PAGE was used to identify molecular weight and purity (see FIG. 10), and SEC detection was performed (see FIG. 11). The amino acid and nucleotide sequences of the heavy chain of the Ps3Vm antibody are SEQ ID NO: 9 and SEQ ID NO: 11, respectively, and the amino acid and nucleotide sequences of the CDR-H1, CDR-H2 and CDR-H3 in the heavy chain variable region are SEQ ID NO: 1-3 and SEQ ID NO: 5-7; the light chain amino acid and nucleotide sequences of the Ps3Vm antibody are SEQ ID NO: 10 and SEQ ID NO: 12, respectively. The amino acid and nucleotide sequences of CDR-L in the light chain variable region are SEQ ID NO: 4 and SEQ ID NO: 8, respectively.

Example 3 Measurement of Affinity of Bispecific Antibodies

1. Affinity of Bispecific Antibody to PD-1

Figure 12:
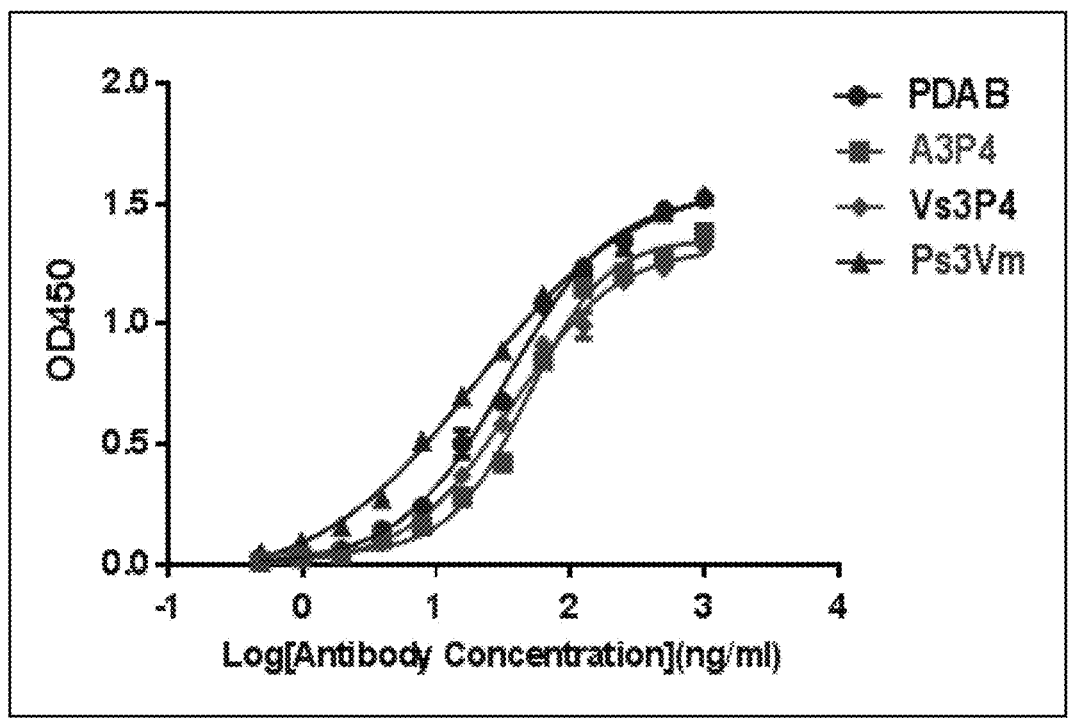
FIG. 12 is a graph showing a comparison of the relative binding activity of PDAB, A3P4, Vs3P4, and Ps3Vm with respect to PD1-His by using ELISA.

The enzyme-labeled plate was coated with PD-1-mFc, blocked with 1% of BSA, and the antibodies PDAB, A3P4, Vs3P4, and Ps3Vm of different concentrations were added to the enzyme-labeled plate respectively. After incubation at 37° C., the enzyme-labeled secondary antibody was added for incubation at 37° C. for 30 minutes. The light absorption value at 450 nm was measured with a microplate reader. The binding result of antibodies PDAB, A3P4, Vs3P4, Ps3Vm and antigen PD-1 showed that antibodies PDAB, A3P4, Vs3P4, and Ps3Vm can effectively bind to PD-1 protein, and the binding efficiency is dose-dependent. The results are shown in FIG. 12 and Table 4.

TABLE 4

Binding efficiency of antibodies PDAB, A3P4, Vs3P4, Ps3Vm and PD-1 protein

| Concentration (ng/mL) | PDAB | | A3P4 | | Vs3P4 | | Ps3Vm | |
|---|---|---|---|---|---|---|---|---|
| 1000 | 1.515 | 1.527 | 1.392 | 1.366 | 1.313 | 1.332 | 1.554 | 1.518 |
| 500 | 1.47 | 1.474 | 1.269 | 1.287 | 1.243 | 1.218 | 1.473 | 1.455 |
| 250 | 1.321 | 1.374 | 1.22 | 1.198 | 1.191 | 1.167 | 1.315 | 1.32 |
| 125 | 1.251 | 1.209 | 1.146 | 1.151 | 1.052 | 0.943 | 1.227 | 1.25 |
| 62.5 | 1.079 | 1.088 | 0.827 | 0.874 | 0.948 | 0.884 | 1.114 | 1.125 |
| 31.25 | 0.684 | 0.674 | 0.443 | 0.409 | 0.597 | 0.574 | 0.893 | 0.89 |
| 15.625 | 0.561 | 0.447 | 0.253 | 0.307 | 0.38 | 0.36 | 0.693 | 0.711 |
| 7.8125 | 0.235 | 0.245 | 0.167 | 0.157 | 0.174 | 0.186 | 0.487 | 0.547 |
| 3.90625 | 0.151 | 0.136 | 0.102 | 0.107 | 0.088 | 0.103 | 0.28 | 0.269 |
| 1.953125 | 0.063 | 0.06 | 0.043 | 0.043 | 0.042 | 0.05 | 0.143 | 0.175 |
| 0.9765625 | 0.038 | 0.032 | 0.034 | 0.03 | 0.023 | 0.028 | 0.081 | 0.112 |
| 0.48828125 | 0.023 | 0.024 | 0.014 | 0.017 | 0.014 | 0.02 | 0.043 | 0.06 |
| EC50 | 33.9 | | 47.92 | | 36.58 | | 20.01 | |

2. Affinity of Bispecific Antibodies to VEGF

Figure 13:
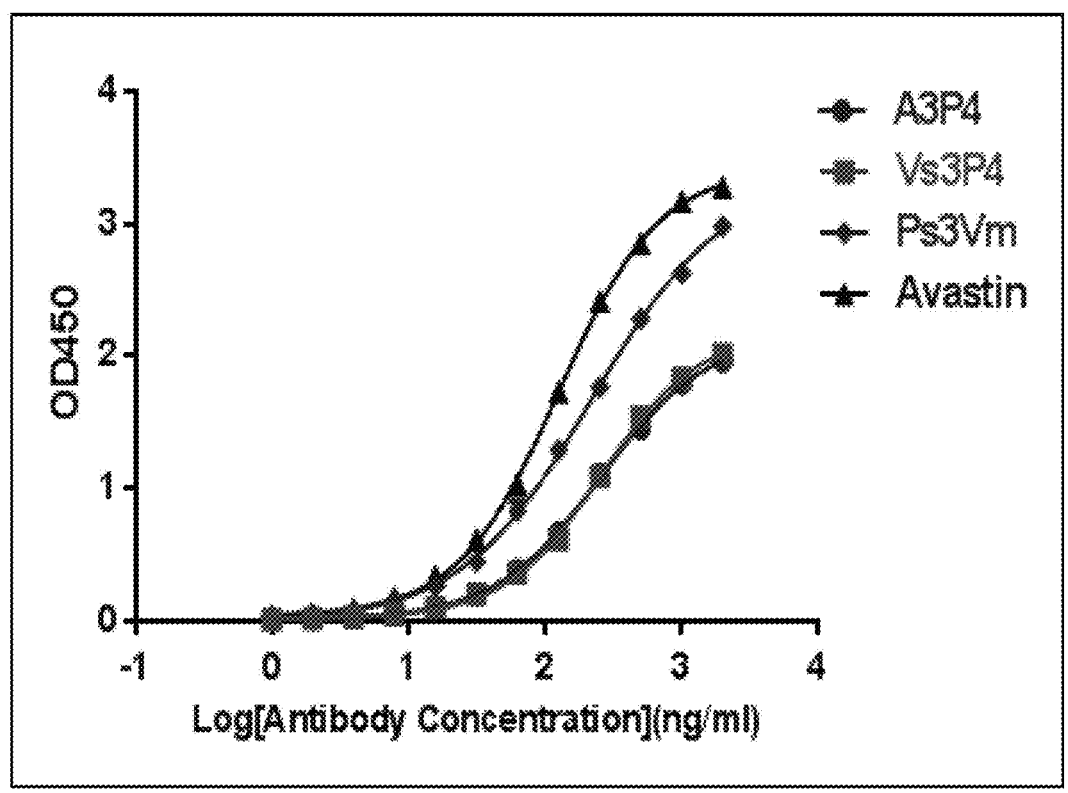
FIG. 13 is a graph showing a comparison of the relative binding activity of Avastin, A3P4, Vs3P4, and Ps3Vm with respect to rHuVEGF by using ELISA.

The enzyme-labeled plate was coated with VEGF-mFc, blocked with 1% of BSA, and the antibodies Avastin, A3P4, Vs3P4, and Ps3Vm of different concentrations were added to the enzyme-labeled plate respectively. After incubation at 37° C., the enzyme-labeled secondary antibody was added for incubation at 37° C. for 30 minutes. The light absorption value at 450 nm was measured with a microplate reader. The binding result of antibodies Avastin, A3P4, Vs3P4, Ps3Vm and antigen VEGF showed that antibodies Avastin, A3P4, Vs3P4, and Ps3Vm can effectively bind to VEGF protein, and the binding efficiency is dose-dependent. The results are shown in FIG. 13 and Table 5.

TABLE 5

Binding efficiency of antibodies Avastin, A3P4, Vs3P4, Ps3Vm and VEGF protein

| Concentration (ng/mL) | Avastin | | A3P4 | | Vs3P4 | | Ps3Vm | |
|---|---|---|---|---|---|---|---|---|
| 2000 | 3.212 | 3.341 | 1.997 | 1.927 | 2.04 | 1.992 | 2.977 | 2.987 |
| 1000 | 3.178 | 3.157 | 1.825 | 1.762 | 1.898 | 1.766 | 2.581 | 2.68 |
| 500 | 2.888 | 2.817 | 1.51 | 1.394 | 1.581 | 1.501 | 2.248 | 2.324 |
| 250 | 2.448 | 2.384 | 1.156 | 1.066 | 1.095 | 1.097 | 1.776 | 1.763 |
| 125 | 1.773 | 1.687 | 0.707 | 0.635 | 0.605 | 0.636 | 1.309 | 1.281 |
| 62.5 | 1.008 | 1.062 | 0.417 | 0.363 | 0.377 | 0.351 | 0.911 | 0.755 |
| 31.25 | 0.619 | 0.617 | 0.212 | 0.196 | 0.208 | 0.199 | 0.47 | 0.433 |
| 15.625 | 0.349 | 0.335 | 0.122 | 0.108 | 0.103 | 0.109 | 0.264 | 0.273 |
| 7.8125 | 0.179 | 0.177 | 0.069 | 0.061 | 0.055 | 0.055 | 0.163 | 0.156 |
| 3.90625 | 0.098 | 0.092 | 0.036 | 0.037 | 0.033 | 0.034 | 0.081 | 0.085 |
| 1.953125 | 0.054 | 0.056 | 0.022 | 0.022 | 0.019 | 0.022 | 0.05 | 0.05 |
| 0.9765625 | 0.035 | 0.036 | 0.013 | 0.016 | 0.016 | 0.016 | 0.039 | 0.049 |
| EC50 | 127.1 | | 258.4 | | 258.7 | | 186.4 | |

Example 4 Measurement of Specificity of Bispecific Antibodies

1. The Specificity of Bispecific Antibodies to PD-1

Figure 14:
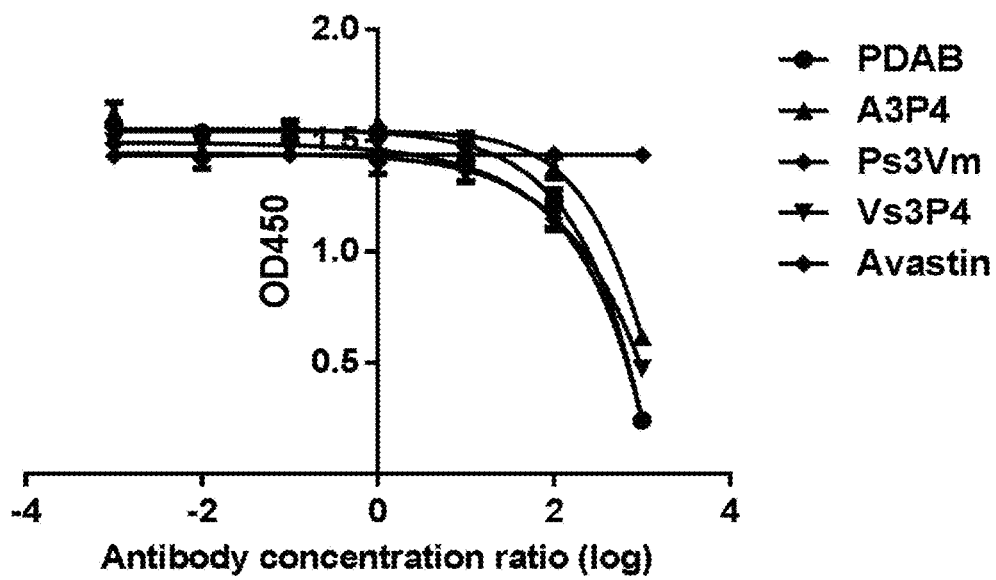
FIG. 14 is a graph showing identification of the specificity of PDAB, A3P4, Vs3P4, Ps3Vm, Avastin and PD1 in binding epitopes by using competitive ELISA.

The enzyme-labeled plate was coated with PD-1-mFc, blocked with 1% of BSA, and the antibodies PDAB, A3P4, Vs3P4, Ps3Vm, and Avastin of different concentrations were mixed with PD-1-mFc, respectively. After incubation at 37° C., the enzyme-labeled secondary antibody was added for incubation at 37° C. for 30 minutes. The light absorption value at 450 nm was measured with a microplate reader. The binding result of antibodies PDAB, A3P4, Vs3P4, Ps3Vm, and Avastin and antigen PD-1 showed that antibodies PDAB, A3P4, Vs3P4, Ps3Vm, and Avastin can effectively compete with PDL-1 to bind to PD-1 protein, and the binding efficiency is dose-dependent. The result is shown in FIG. 14.

2. Specificity of Bispecific Antibodies to VEGF

Figure 15:
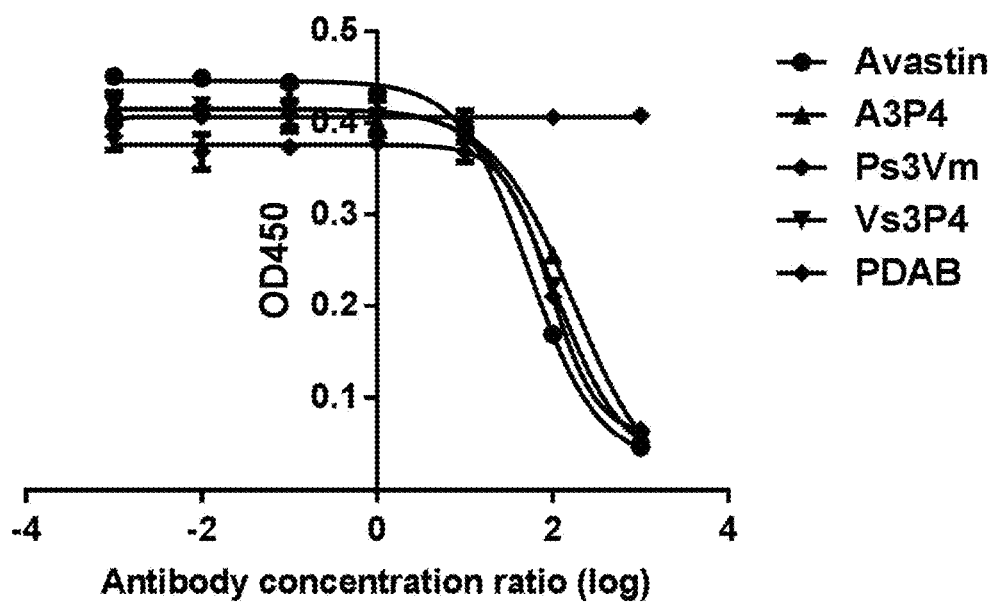
FIG. 15 is a graph showing identification of the specificity of PDAB, A3P4, Vs3P4, Ps3Vm, Avastin and VEGF in binding epitopes by using competitive ELISA.

The enzyme-labeled plate was coated with VEGF-mFc, blocked with 1% of BSA, and the antibodies Avastin, A3P4, Vs3P4, Ps3Vm, and PDAB of different concentrations were mixed with VEGF-A-hFc, respectively. After incubation at 37° C., the enzyme-labeled secondary antibody was added for incubation at 37° C. for 30 minutes. The light absorption value at 450 nm was measured with a microplate reader. The binding result of antibodies Avastin, A3P4, Vs3P4, Ps3Vm, and PDAB and antigen VEGF showed that antibodies Avastin, A3P4, Vs3P4, Ps3Vm, and PDAB can effectively compete with VEGF-A to bind to VEGF protein, and the binding efficiency is dose-dependent. The result is shown in FIG. 15.

Figure 16:
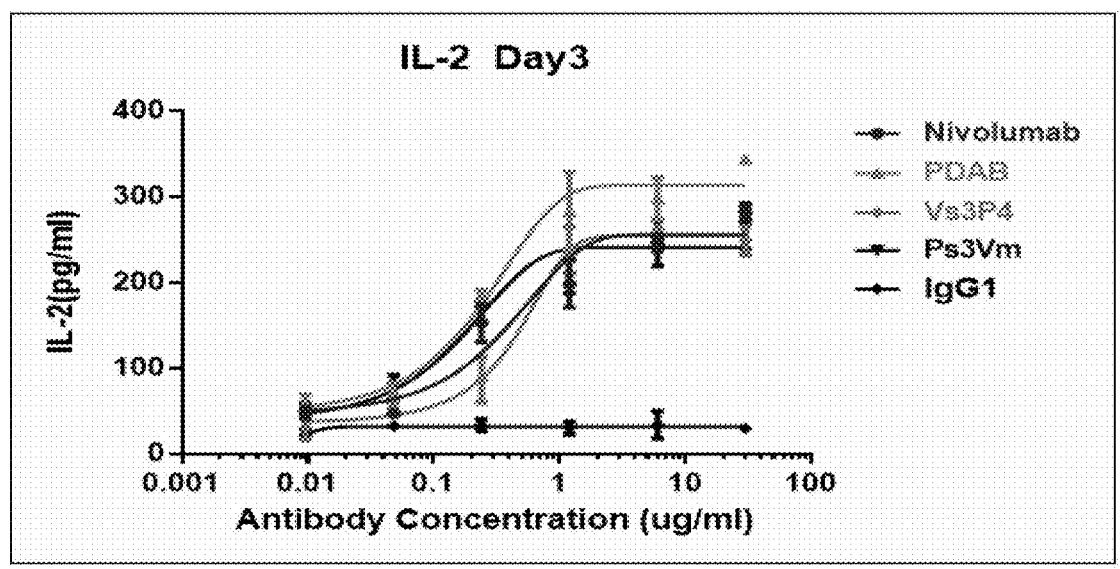
FIG. 16 is a graph showing the change of amount of IL-2 secreted by T cells induced by Nivolumab, PDAB, Vs3P4, Ps3Vm, and IgG1 in vitro in relation to the change of concentration of antibody.

Example 5 Candidate Bispecific Antibodies Induce T Cells to Secrete IL-2 In Vitro The Ficoll centrifugation method (purchased from GE) and CD4+ T cell enrichment column (purchased from R&D Systems) were used to prepare fresh PBMC and purify human T cells. Plate the cells into a 96-well flat bottom plate, after overnight cultivation, add six different concentrations of antibodies NIVO, PDAB, Vs3P4 and Ps3Vm in an amount of 0.0096, 0.048, 0.24, 1.2, 6, and 30 µg/mL respectively. The same type control antibody IgG1 of six different concentrations were added as a negative control. After 3 days of culture, the supernatant was collected, and the secretion level of the supernatant IL-2 was measured by using a Luminex apparatus (purchased from LifeTechnology) and a cytokine IL-2 detection kit (purchased from BD Biosciences). The result is shown in FIG. 16. The result showed that the bispecific antibodies Vs3P4 and Ps3Vm can effectively stimulate the function of T cells to secrete the cytokine IL-2, and the stimulation is related to antibody concentration, whereas the isotype control antibody cannot promote proliferation of T cells and secretion of IL-2.

Figure 17:
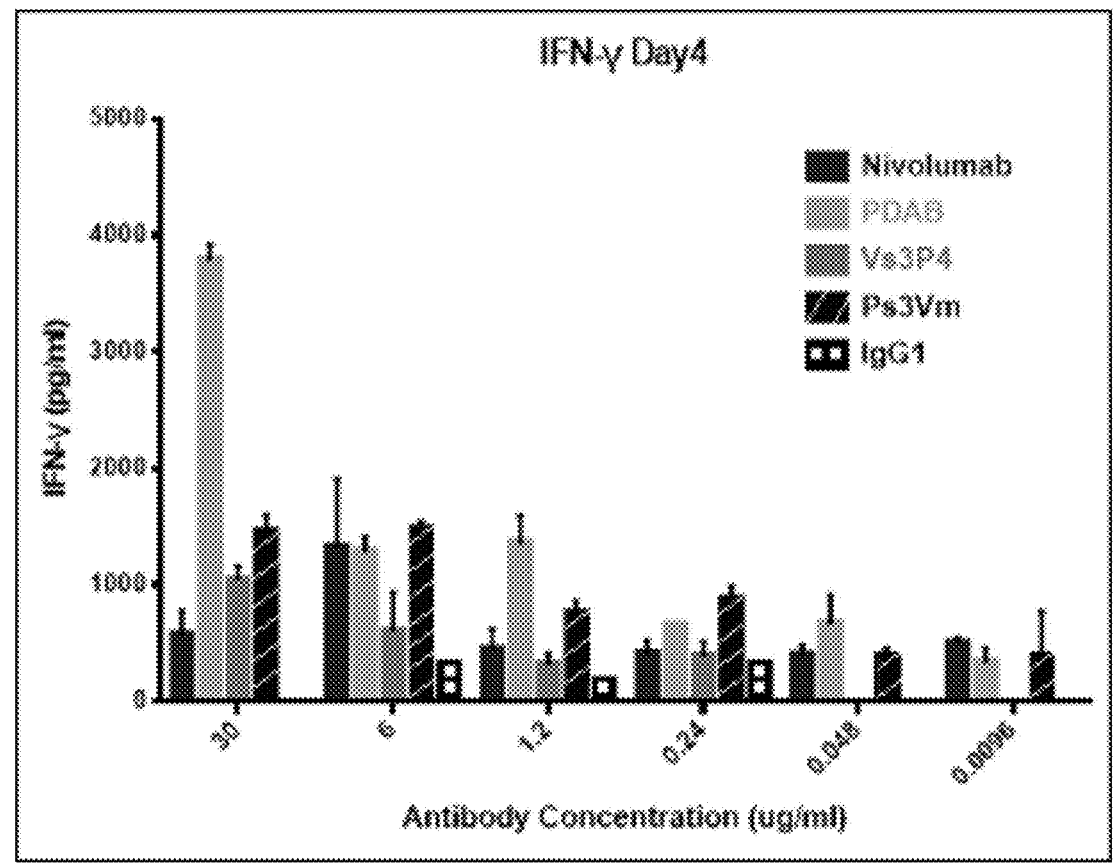
FIG. 17 is a graph showing the change of amount of IFN-γ secreted by T cells induced by Nivolumab, PDAB, Vs3P4, Ps3Vm, and IgG1 in vitro in relation to the change of concentration of antibody.

Example 6 Candidate Bispicific Antibodies Induce T Cells to Secrete IFN-γ In Vitro The Ficoll centrifugation method (purchased from GE) and CD4+ T cell enrichment column (purchased from R&D Systems) were used to prepare fresh PBMC and purify human T cells. The monocytes were purified by using Miltenyi CD14 monocyte purification kit, and DC cells were generated after monocytes were cultured with GM-CSF and IL-4 (both purchased from PeproTech) for 7 days. Plate the cells into a 96-well flat bottom plate, after overnight cultivation, each culture with a total volume of 200 μL contains 10e5 purified T cells and 10e4 dendritic cells. Add six different concentrations of antibodies NIVO, PDAB, Vs3P4 and Ps3Vm in an amount of 0.0096, 0.048, 0.24, 1.2, 6, and 30 μg/mL respectively. The same type control antibody IgG1 of six different concentrations were added as a negative control. The cells were cultured for 5 days at 37° C. After 5 days, 100 μL of culture medium was taken from each culture for measurement of cytokine IFN-γ. The level of IFN-γ was measured by using OptEIA ELISA kit (purchased from BD Biosciences). The result is shown in FIG. 17. The result showed that the bispecific antibodies Vs3P4 and Ps3Vm can effectively stimulate the function of T cells to secrete the cytokine IFN-γ, and the stimulation is related to concentration, whereas the isotype control antibody cannot promote proliferation of T cells and secretion of IFN-γ.

Example 7 Candidate Bispecific Antibody Inhibits Tumor Growth in Mice

1. Preliminarily Constructed Mouse Model, Select PBMC Cells Suitable for the Experiment The PBMC cells, human colon cancer Colo-205 cells, B-NDG mice used in this experiment are commonly available in the industry.

Human colon cancer Colo-205 cells purchased from the Chinese Academy of Sciences were cultured above $6.0*10^7$, and B-NDG mice ($2.0*10^6$ cells each, 30 mice in total) subcutaneously inoculated with the cells were purchased from Biocytogen. The mice were fed normally, and when the tumor grew to a size of 100 mm³, the human PBMC cells purchased from different sources were intraperitoneally injected into each of the B-NDG severely immunodeficient mice purchased from Biocytogen at $1*10^7$. The growing condition of the tumor was observed until the tumor was formed successfully (select 10 groups of PBMC cells and inject each group of the cells into 3 mice for parallel experiments).

Figure 18:
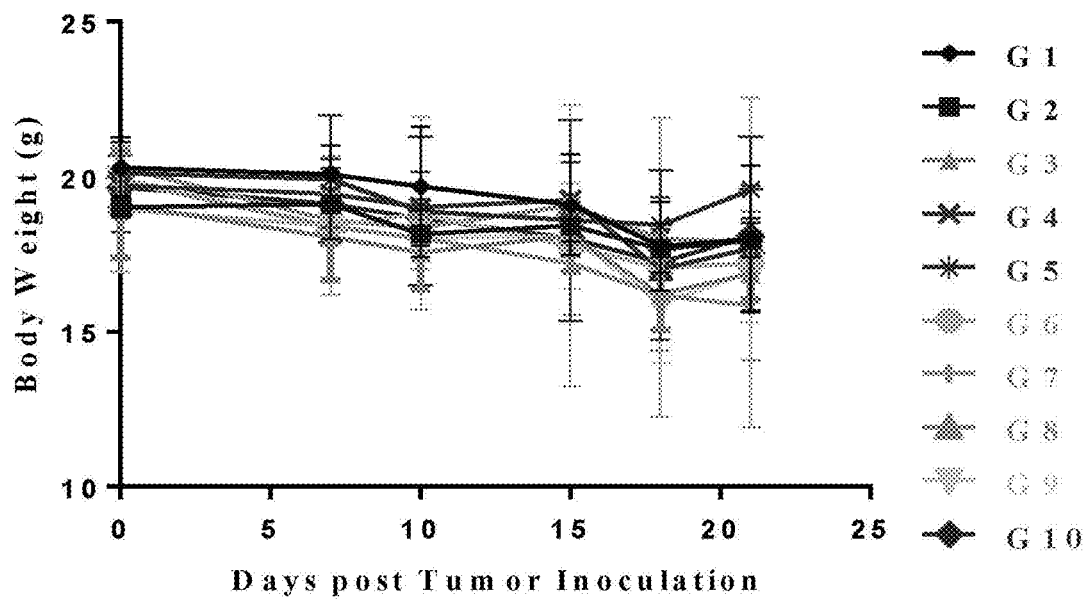
FIG. 18 is a graph showing the weight change of a mouse model initially constructed.
Figure 19:
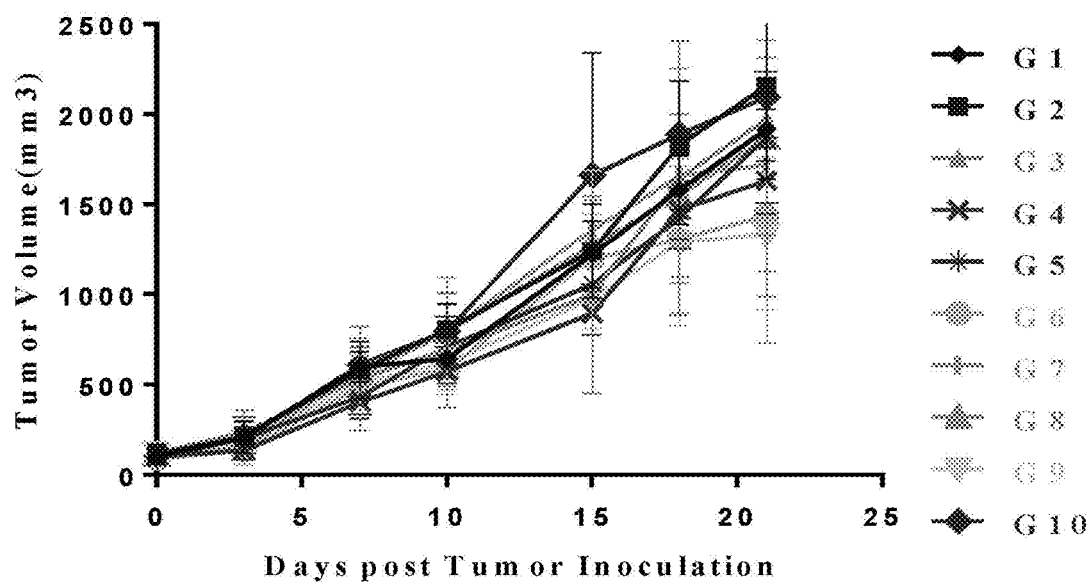
FIG. 19 is a graph showing the change of tumor volume of a mouse model initially constructed.

The experimental results are shown in Table 6 below and FIG. 18 and FIG. 19 (all figures are averages):

TABLE 6

Change of weight and tumor size in preliminarily constructed mouse model

| | | DAY | | | | | | |
|---|---|---|---|---|---|---|---|---|
| | | 0 | 3 | 7 | 10 | 15 | 18 | 21 |
| G1 | Body Weight (g) | 20.30 | 20.20 | 20.10 | 19.70 | 19.10 | 17.77 | 18.00 |
| | Tumor Size (mm³) | 102.73 | 209.05 | 599.98 | 644.22 | 1223.34 | 1581.46 | 1918.73 |
| G2 | Body Weight (g) | 19.03 | 19.07 | 19.13 | 18.17 | 18.43 | 17.70 | 17.97 |
| | Tumor Size (mm³) | 116.63 | 214.43 | 579.18 | 805.71 | 1242.41 | 1830.42 | 2160.05 |
| G3 | Body Weight (g) | 19.10 | 18.56 | 18.07 | 17.57 | 18.10 | 16.23 | 16.90 |
| | Tumor Size (mm³) | 121.03 | 237.41 | 534.89 | 692.74 | 999.83 | 1647.12 | 1974.83 |
| G4 | Body Weight (g) | 19.73 | 19.65 | 19.47 | 19.03 | 19.27 | 17.03 | 17.70 |
| | Tumor Size (mm³) | 103.10 | 138.20 | 404.44 | 575.30 | 897.40 | 1471.85 | 1634.99 |
| G5 | Body Weight (g) | 20.13 | 20.01 | 19.93 | 18.90 | 18.60 | 18.45 | 19.60 |
| | Tumor Size (mm³) | 100.92 | 205.06 | 432.67 | 709.04 | 1056.45 | 1425.82 | 1872.85 |
| G6 | Body Weight (g) | 18.97 | 18.74 | 18.43 | 18.83 | 17.77 | 17.07 | 17.23 |
| | Tumor Size (mm³) | 93.56 | 137.69 | 487.36 | 591.19 | 1199.08 | 1307.07 | 1439.73 |

TABLE 6-continued

Change of weight and tumor size in preliminarily constructed mouse model

| | | DAY | | | | | | |
|---|---|---|---|---|---|---|---|---|
| | | 0 | 3 | 7 | 10 | 15 | 18 | 21 |
| G7 | Body Weight (g) | 19.90 | 19.05 | 18.40 | 18.03 | 17.23 | 16.20 | 15.87 |
| | Tumor Size (mm³) | 109.67 | 153.39 | 590.91 | 794.74 | 1358.81 | 1660.09 | 1721.64 |
| G8 | Body Weight (g) | 20.33 | 19.13 | 18.60 | 18.37 | 19.10 | 18.00 | 15.10 |
| | Tumor Size (mm³) | 115.43 | 211.55 | 555.03 | 793.15 | 1273.73 | 1550.99 | 1872.78 |
| G9 | Body Weight (g) | 19.97 | 19.20 | 18.43 | 18.03 | 18.10 | 15.93 | 16.93 |
| | Tumor Size (mm³) | 120.50 | 180.85 | 511.27 | 619.23 | 978.95 | 1290.83 | 1339.49 |
| G10 | Body Weight (g) | 19.67 | 19.53 | 19.13 | 18.67 | 18.03 | 17.25 | 18.10 |
| | Tumor Size (mm³) | 108.68 | 197.87 | 611.62 | 797.08 | 1662.81 | 1891.89 | 2096.03 |

2. Use the Selected PBMC Cells to Build Animal Models

PBMC cells (G1, G2, G8, G10) with successful matching were selected and injected into B-NDG-b2m MHC knockout severely deficient mice (1*10⁷ cells per mouse) purchased from Biocytogen. Meanwhile, the mice were subcutaneously inoculated with human colon cancer Colo-205 cells to observe whether tumors are formed successfully, which is a pre-experiment. Only 8 mice were injected and inoculated (as two sets of parallel experiments). Tumorigenicity was observed and the PBMC cells that were successfully formed into tumors were selected for the next stage of experiment.

The change in tumor size is shown in Table 7 below (all numbers are averages in the table): Tumor Volume (mm³)

TABLE 7

Tumor volume changes of constructed animal model with selected PBMC cells

| | DAY | | | | | | |
|---|---|---|---|---|---|---|---|
| | 0 | 3 | 7 | 10 | 15 | 18 | 21 |
| G1 | 100.23 | 230.56 | 548.73 | 668.39 | 1268.45 | 1684.54 | 2025.68 |
| G2 | 108.35 | 203.21 | 502.72 | 851.94 | 1054.26 | 1563.81 | 1954.29 |

TABLE 7-continued

Tumor volume changes of constructed animal model with selected PBMC cells

| | DAY | | | | | | |
|---|---|---|---|---|---|---|---|
| | 0 | 3 | 7 | 10 | 15 | 18 | 21 |
| G8 | 113.51 | 211.55 | 465.84 | 712.43 | 946.25 | 1458.48 | 1743.65 |
| G10 | 100.62 | 198.36 | 600.26 | 900.25 | 1356.31 | 1965.32 | 2200.25 |

3. Animal Model Construction for Experiments

The above PBMC cells (G10) were selected and injected into B-NDG-b2m MHC knockout severely deficient mice (1*10⁷ cells per mouse in 4 groups, 6 mice per group) purchased from Biocytogen. Meanwhile, the mice were subcutaneously inoculated with human colon cancer Colo-205 cells to observe whether tumors are formed successfully. The mice were randomly divided into 4 groups according to growth of tumor. Negative control group (intraperitoneally injected with saline), Vs3P4 group (subjected to tail vein injection of Vs3P4 antibody in an amount of 3 mg/kg), Ps3Vm group (subjected to tail vein injection of Ps3Vm antibody in an amount of 3 mg/kg), positive control group bevacizumab (subjected to tail vein injection in an amount of 3 mg/kg). The mice were administered with dose every 3 days for a total of 21 days. The tumor volume changes are shown in the table below: Tumor Volume (mm³)

TABLE 8

Tumor volume changes in animal models for experiments

| | Days | | | | | | |
|---|---|---|---|---|---|---|---|
| | 0 | 3 | 7 | 10 | 15 | 18 | 21 |
| Saline | 400.23 | 609.56 | 812.26 | 1009.32 | 1478.26 | 1993.54 | 2365.82 |
| Vs3P4 | 403.26 | 454.35 | 353.02 | 256.51 | 202.56 | 194.32 | 203.45 |
| Ps3Vm | 400.24 | 469.35 | 260.24 | 134.87 | 108.46 | 156.36 | 147.51 |
| Avastin antibody | 408.58 | 498.69 | 338.56 | 305.45 | 289.5 | 306.43 | 324.62 |

The disclosure tested anti-VEGF-PD1 bispecific antibodies with three different structures, and respectively tested their antibody effects from molecular, cellular, biological aspects. The results show that: bispecific antibody Ps3Vm (with VEGF as the skeleton with insertion of dsFv-PD1 monomer) has the best test effect, can effectively bind to PD-1 and VEGF protein, and can effectively compete with PDL-1 to bind to PD-1 protein and compete with VEGF-A to bind to VEGF protein, while can effectively stimulate the function of T cells and secretion of cytokines IL-2 and IFN-γ. In contrast, the isotype control antibody cannot promote proliferation of the T cells and secretion of IL-2 and IFN-γ. In addition, the bispecific antibody Ps3Vm can also significantly inhibit growth of tumor in mice.

Although the disclosure has been disclosed in the above embodiments, it is not intended to limit the disclosure, and those skilled in the art can make some modifications and refinements without departing from the spirit and scope of the disclosure. Therefore, the scope of the disclosure is subject to the definition of the scope of the appended claims.

What is claimed is:

1. An anti-VEGF-PD1 bispecific antibody Ps3Vm comprising the dsFv-PD1-linker-VEGF-H chain structure of SEQ ID NO: 9 and the anti-VEGF light chain of SEQ ID NO: 10.

2. A pharmaceutical composition comprising the bispecific antibody of claim 1 and a pharmaceutically acceptable carrier.

* * * * *